US009708397B2

(12) United States Patent
Greenwood et al.

(10) Patent No.: US 9,708,397 B2
(45) Date of Patent: Jul. 18, 2017

(54) TREATMENT OF VASCULOPROLIFERATIVE CONDITIONS WITH LRG1 ANTAGONISTS

(71) Applicant: UCL Business PLC, London (GB)

(72) Inventors: John Greenwood, London (GB); Stephen Moss, London (GB); Xiaomeng Wang, London (GB)

(*) Notice: Subject to any disclaimer, the term of this patent is extended or adjusted under 35 U.S.C. 154(b) by 0 days.

(21) Appl. No.: 14/312,593

(22) Filed: Jun. 23, 2014

(65) Prior Publication Data

US 2014/0377277 A1    Dec. 25, 2014

Related U.S. Application Data

(62) Division of application No. 13/393,531, filed as application No. PCT/GB2010/001681 on Sep. 6, 2010, now Pat. No. 8,790,647.

(51) Int. Cl.

| C12N 15/11 | (2006.01) |
|---|---|
| C07K 16/22 | (2006.01) |
| C07K 14/47 | (2006.01) |
| C07K 14/495 | (2006.01) |
| C07K 16/18 | (2006.01) |
| C12N 15/113 | (2010.01) |
| A61K 39/00 | (2006.01) |

(52) U.S. Cl.
CPC ............. *C07K 16/22* (2013.01); *C07K 14/47* (2013.01); *C07K 14/495* (2013.01); *C07K 16/18* (2013.01); *C12N 15/113* (2013.01); *C12N 15/1136* (2013.01); *A61K 2039/505* (2013.01); *C07K 2317/76* (2013.01); *C12N 2310/14* (2013.01); *C12N 2310/141* (2013.01); *C12N 2320/30* (2013.01)

(58) Field of Classification Search
CPC .......................... C12N 15/113; C12N 2310/141
See application file for complete search history.

(56) References Cited

U.S. PATENT DOCUMENTS

| 2005/0064516 | A1 | 3/2005 | Kantor et al. | |
|---|---|---|---|---|
| 2007/0184503 | A1 | 8/2007 | Jemmerson | |
| 2009/0163434 | A1* | 6/2009 | Bader | C12N 15/111 514/44 R |
| 2009/0163435 | A1* | 6/2009 | Bader | C12N 15/111 514/44 R |
| 2009/0175827 | A1* | 7/2009 | Byrom | A61K 31/7088 424/93.2 |
| 2009/0192111 | A1* | 7/2009 | Bader | C12N 15/113 514/44 R |
| 2009/0227533 | A1* | 9/2009 | Bader | C12N 15/113 514/44 R |

FOREIGN PATENT DOCUMENTS

| WO | WO-00/01410 | 1/2000 |
|---|---|---|
| WO | WO-2007/040912 | 4/2007 |
| WO | WO-2008/092214 | 8/2008 |
| WO | WO-2009/061807 | 5/2009 |
| WO | WO-2011/015602 | 2/2011 |

OTHER PUBLICATIONS

Lynch et al. Carcinogenesis 33, 976-985, 2012.*
Chang et al., "Characterization of two genes encoding leucin-rich repeat-containing proteins in grass carp *Ctenopharyngodon idellus*," Immunogenetics (2005) 56:710-721.
Cheung et al., "The HCV serum proteome: a search for fibrosis protein markers," Journal of Viral Hepatitis (2009) 16:418-429.
Clemons et al., "The National Eye Institute Visual Function Questionnaire in the Macular Telangiectasia (MacTel) Project," Investigative Ophthalmology & Visual Science (2008) 49(10):4340-4346.
Cummings et al., "Serum leucine-rich alpha-2-glycoprotein-1 binds cytochrome c and inhibits antibody detection of this apoptotic marker in enzyme-linked immunosorbent assay," Apoptosis (2006) 11:1121-1129.
Ferrero et al., "Increased expression of one isoform of leucine-rich alpha-2-glycoprotein in peritoneal fluid of women with uterine leiomyomas," Arch. Gynecol. Obstet. (2009) 279(3):365-371.
Goumans et al., "Controlling the angiogenic switch: a balance between two distinct TGF-b receptor signaling pathways," Trends in Cardiovascular Medicine (2003) 13(7):301-307.
Govorukhina et al., "Influence of clotting time on the protein composition of serum samples based on LC-MS data," Journal of Chromotagraphy B (2009) 877:1281-1291.
Haupt et al., "Isolation and characterization of an unknown, leucine-rich 3,1-S-alpha2-glycoprotein from human serum," Physiol. Chem. (1977) 358(6):639-646.
Heo et al., "Identification of putative serum glycoprotein biomarkers for human lung adenocarcinoma by multilectin affinity chromatography and LC-MS/MS," Proteomics (2007) 7(23):4292-4302.
International Preliminary Report on Patentability for PCT/GB2010/001681, mailed Mar. 6, 2012, 10 pages.
International Search Report for PCT/GB2010/001681, mailed Dec. 16, 2010, 3 pages.
Johnson et al., "A second locus for hereditary hemorrhagic telangiectasia maps to chromosome 12," Genome Res. (1995) 5(1):21-28.
Kakisaka et al., "Plasma proteomics of pancreatic cancer patients by multi-dimensional liquid chromatography and two-dimensional difference gel electrophoresis (2D-DIGE): up-regulation of leucine-rich alpha-2-glycoprotein in pancreatic cancer," J. Chromatogr. B Analst Technol Biomed Life Sci (2007) 852(1-2):257-267.

(Continued)

*Primary Examiner* — Brian Whiteman
(74) *Attorney, Agent, or Firm* — Morrison & Foerster LLP

(57) ABSTRACT

This invention relates to the field of molecular physiology. Specifically, this invention relates to the treatment of vasculoproliferative conditions, especially those of the eye and in the treatment of tumours that exhibit vascular proliferation. Levels of leucine-rich alpha-2-glycoprotein (Lrg1) have been demonstrated to be increased in patients suffering from such conditions and animal models of such conditions. Antagonists of Lrg1 can be used to treat vasculoproliferative conditions.

8 Claims, 18 Drawing Sheets

(56) References Cited

OTHER PUBLICATIONS

Kentsis et al., "Discovery of Validation of Urine Markers of Acute Pediatric Appenddicitis Using High-Accuracy Mass Spectrometry," Annals of Emergency Medicine (2009) 1-13.

Khositseth et al., "IgA nephropathy associated with Hodgkin's disease in children: a case report, literature review and urinary proteome analysis," Pediatr. Nephrol. (2007) 22:541-546.

Kitaguchi et al., "Characterization of the Gene Encoding Mouse Platelet Glycoprotein Ibβ," Thrombosis Research (1997) 87(2):235-244.

Li et al., "Analysis of potential diagnostic biomarkers in cerebrospinal fluid of idiopathic normal pressure hydrocephalus by proteomics," Acta Neurochir. (2006) 148:859-864.

Li et al., "Expression of TGF-betas and TGF-beta type II receptor in cerebrospinal fluid of patients with idiopathic normal pressure hydrocephalus," Neurosci. Lett. (2007) 413(2):141-144.

Marchuk et al., "Vascular morphogenesis: tales of two syndromes," Human Molecular Genetics (2003) 12(1):R97-112.

McAllister et al., "Endoglin, a TGF-beta binding protein of endothelial cells, is the gene for hereditary haemorrhagic telangiectasia type 1," Nat. Genet. (1994) 8(4):345-351.

Norkina et al., Am. J. Physiol. Gastrointest. Liver Physiol. (2004) 286:G1032-G1041.

Saito et al., "Gene Expression Profiling of Mucosal Addressin Cell Adhesion Molecule-1+ High Endothelial Venule Cells (HEV) and Identification of a Leucine-Rich HEV Glycoprotein as a HEV Marker," The Journal of Immunology (2002) 168:1050-1059.

Schwick et al., "Purified Human Plasma Proteins of Unknown Function," Japan J. Med. Sci. Biol. (1981) 34:299-327.

Shirai et al., "Up-regulation of the expression of leucine-rich α2-glycoprotein in hepatocytes by the mediators of acute-phase response," Biochemical and Biophsyical Research Communications (2009) 382:776-779.

Spirin et al., "Basement membrane and growth factor gene expression in normal and diabetic human retinas," Curr. Eye Res. (1999) 18(6):490-499.

Sun et al., "Differentially expressed genes in TGF-beta 1 sensitive and resistant human hematoma cells," Cancer Lett. (1995) 89(1):73-79.

Sviridov et al., "Proteinuria without albuminuria: Urinary protein excretion by a subset of patients with burn injuries," Clinica Chimica Acta (2009) 403:42-46.

Takahashi et al., "Purification of glycopeptides of human plasma proteins by high-performance liquid chromatography," Journal of Chromatography (1984) 317:11-26.

Takahashi et al., "Periodicity of leucine and tandem repetition of a 24-amino acid segment in the primary structure of leucine-rich alpha 2-glycoprotein of human serum," PNAS USA (1985) 82(7):1906-1910.

Ten Dijke et al., "Extracellular control of TGFβ signalling in vascular development and disease," Nature Reviews (2007) 8:857-869.

Weivoda et al., "ELISA for human serum leucine-rich alpha-2-glycoprotein-1 employing cytochrome c as the capturing ligand," Journal of Immunological Methods (2008) 336:22-29.

Zeng et al., "Utilizing 2-DE and MALDI-TOF MS/MS to screen differentially expressed serum proteins of silicosis," Zhonghua Lao Dong Wei Sheng Zhi Ye Bing Za Zhi (2007) 25(3):136-141.

Zhang et al., "Potential diagnostic biomarkers in serum of idiopathic pulmonary arterial hypertension," Respir. Med. (Aug. 22, 2009) [Epub ahead of print].

* cited by examiner

A
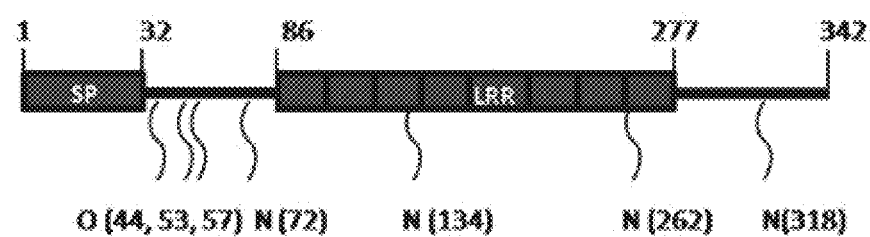
B
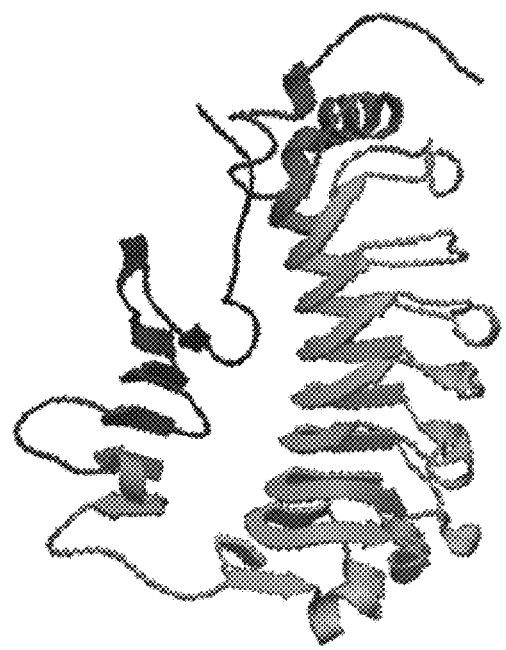
Figure 2

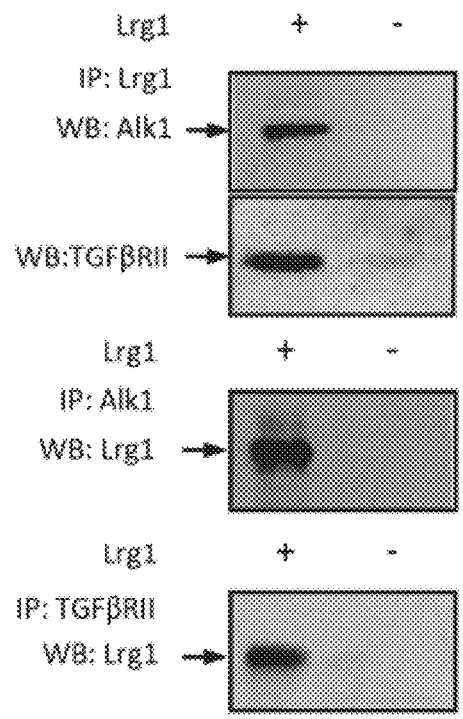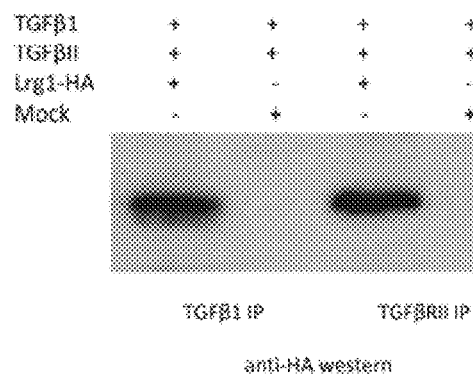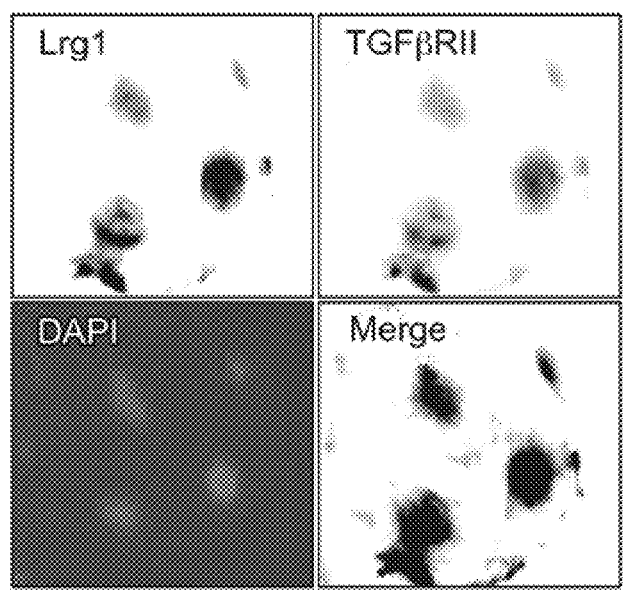
Figure 4 A to C

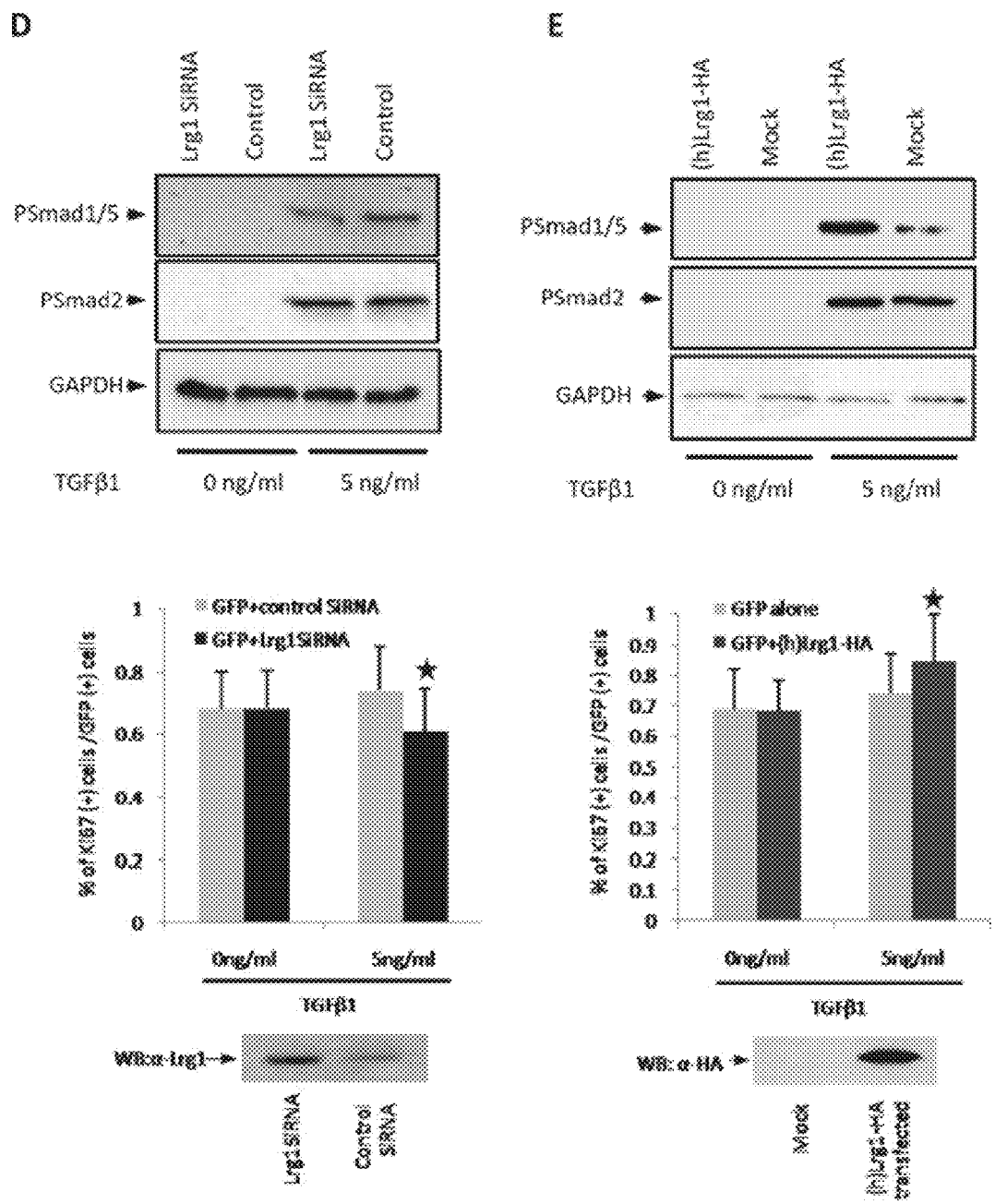
Figure 4 (continued) D and E

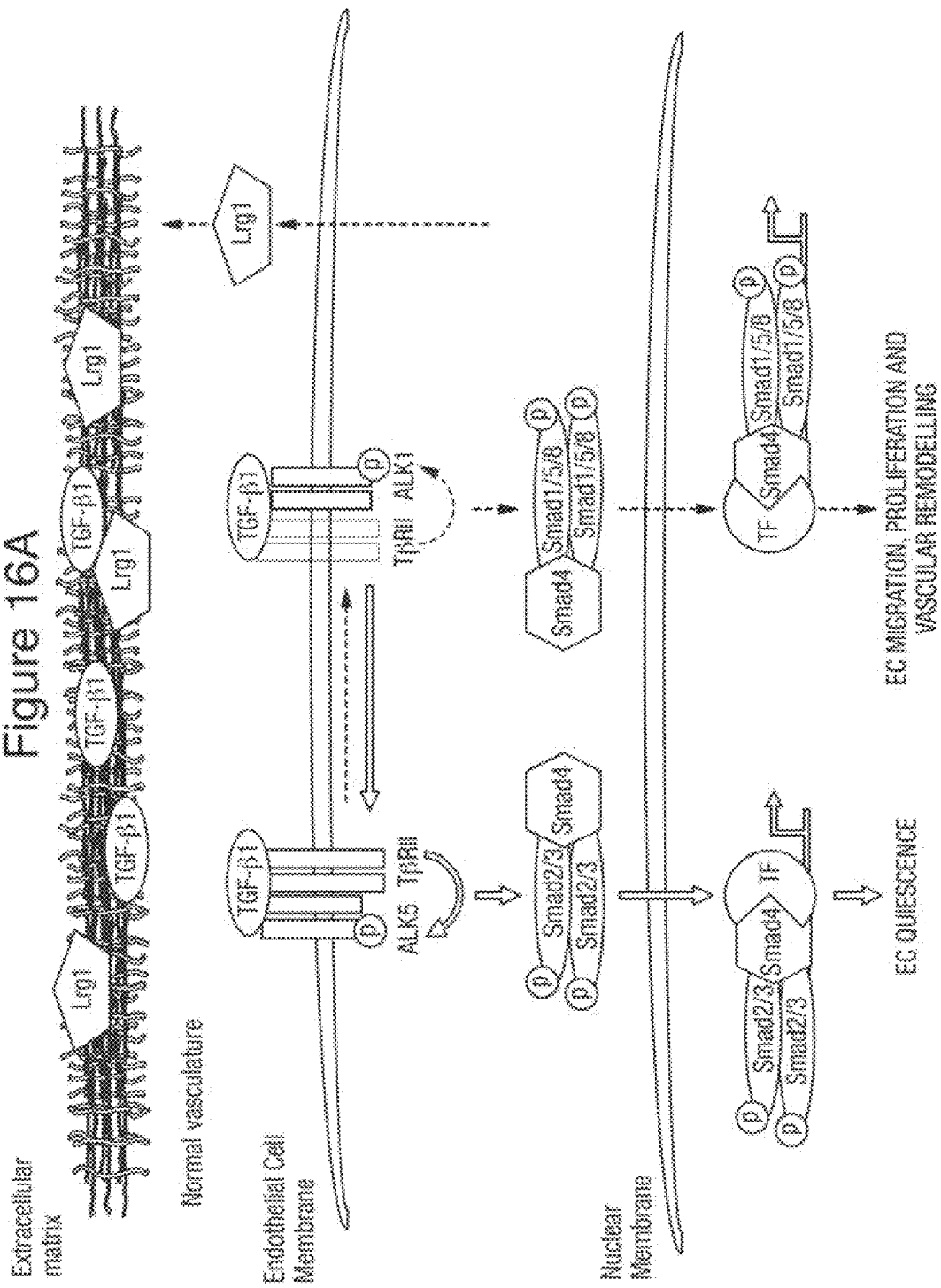

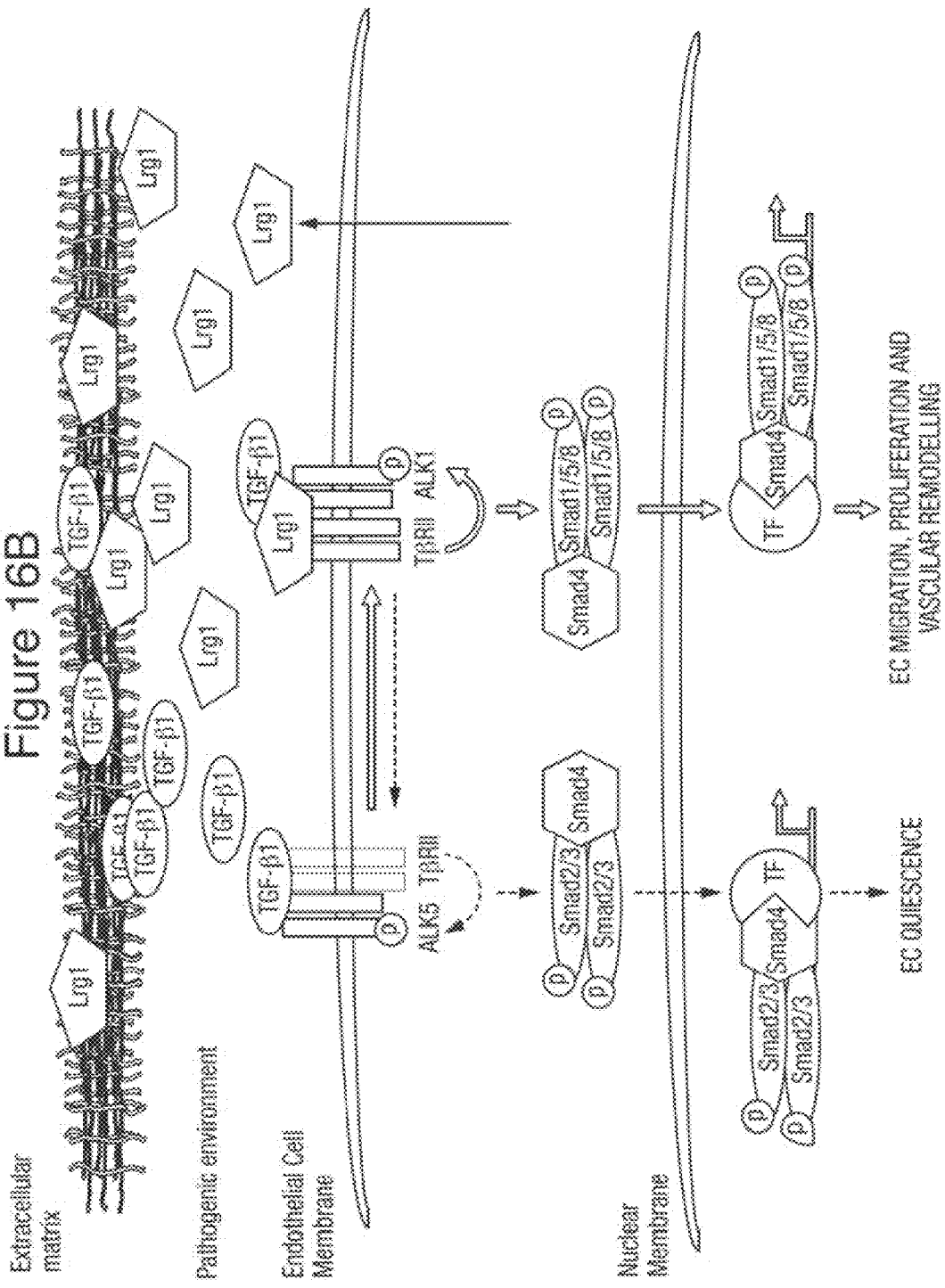

SEQUENCE LISTING

<160> NUMBER OF SEQ ID NOS: 9

<210> SEQ ID NO 1
<211> LENGTH: 1780
<212> TYPE: DNA
<213> ORGANISM: Homo sapiens

<400> SEQUENCE: 1

```
gcagagctac catgtcctct tggagcagac agcgaccaaa aagcccaggg ggcattcaac      60
cccatgtttc tagaactctg ttcctgctgc tgctgttggc agcctcagcc tggggggtca     120
ccctgagccc caaagactgc caggtgttcc gctcagacca tggcagctcc atctcctgtc     180
aaccacctgc cgaaatcccc ggctacctgc cagccgacac cgtgcacctg gccgtggaat     240
tcttcaacct gacccacctg ccagccaacc tcctccaggg cgcctctaag ctccaagaat     300
tgcacctctc cagcaatggg ctggaaagcc tctcgcccga attcctgcgg ccagtgccgc     360
agctgagggt gctggatcta ccgaaacg ccctgaccg gctgccccg ggcctcttcc      420 aggcctcagc caccctggac accctggtat tgaaagaaaa ccagctggag gtcctggagg     480
tctcgtggct acacggcctg aaagctctgg gcatctgga cctgtctggg aaccgcctcc     540
ggaaactgcc ccccgggctg ctggccaact tcaccctcct gcgcacccct gaccttgggg     600
agaaccagtt ggagaccttg ccacctgacc tcctgagggg tccgctgcaa ttagaacggc     660
tacatctaga aggcaacaaa ttgcaagtac tgggaaaaga tctcctcttg ccgcagccgg     720
acctgcgcta cctcttcctg aacggcaaca agctggccag ggtggcagcc ggtgccttcc     780
agggcctgcg gcagctggac atgctggacc tctccaataa ctcactggcc agcgtgcccg     840
aggggctctg gcatcccta gggcagccaa actgggacat gcgggatggc ttcgacatct     900
ccggcaaccc ctggatctgt gaccagaacc tgagcgacct ctatcgttgg cttcaggccc     960
aaaaagacaa gatgttttcc cagaatgaca cgcgctgtgc tgggcctgaa gccgtgaagg    1020
gccagacgct cctggcagtg gccaagtccc agtgagacca ggggcttggg ttgagggtgg    1080
ggggtctggt agaacactgc aacccgctta caaataatc ctgcctttgg ccgggtgcgg     1140
gggctcacgc ctgtaatccc agcactttgg gaggcccagg tggcggatc acgaggtcag     1200 gagatcgaga ccatcttggc taacatggtg aaaccctgtc tctactaaaa atataaaaaa     1260
```

-continued

```
ttagccaggc gtggtggtgg gcacctgtag tcccagcaac tcgggaggct gaggcaggag    1320
aatggcgtga acttgggagg cggagcttgc ggtgagccaa gatcgtgcca ctgcactcta    1380
gcctgggcga cagagcaaga ctgtctcaaa aaaattaaaa ttaaaattaa aaacaaataa    1440
tcctgccttt tacaggtgaa actcggggct gtccatagcg gctgggaccc cgtttcatcc    1500
atccatgctt cctagaacac acgatgggct ttccttaccc atgcccaagg tgtgccctcc    1560
gtctggaatg ccgttccctg tttcccagat ctcttgaact ctgggttctc ccagcccctt    1620
gtccttcctt ccagctgagc cctggccaca ctggggctgc ctttctctga ctctgtcttc    1680
cccaagtcag ggggctctct gagtgcaggg tctgatgctg agtcccactt agcttggggt    1740
cagaaccaag gggtttaata aataacccctt gaaaactgga                         1780
```

<210> SEQ ID NO 2
<211> LENGTH: 347
<212> TYPE: PRT
<213> ORGANISM: Homo sapiens

<400> SEQUENCE: 2

```
Met Ser Ser Trp Ser Arg Gln Arg Pro Lys Ser Pro Gly Gly Ile Gln
1               5                   10                  15

Pro His Val Ser Arg Thr Leu Phe Leu Leu Leu Leu Ala Ala Ser
            20                  25                  30

Ala Trp Gly Val Thr Leu Ser Pro Lys Asp Cys Gln Val Phe Arg Ser
        35                  40                  45

Asp His Gly Ser Ser Ile Ser Cys Gln Pro Pro Ala Glu Ile Pro Gly
    50                  55                  60

Tyr Leu Pro Ala Asp Thr Val His Leu Ala Val Glu Phe Phe Asn Leu
65                  70                  75                  80

Thr His Leu Pro Ala Asn Leu Leu Gln Gly Ala Ser Lys Leu Gln Glu
                85                  90                  95

Leu His Leu Ser Ser Asn Gly Leu Glu Ser Leu Ser Pro Glu Phe Leu
            100                 105                 110

Arg Pro Val Pro Gln Leu Arg Val Leu Asp Leu Thr Arg Asn Ala Leu
        115                 120                 125

Thr Gly Leu Pro Pro Gly Leu Phe Gln Ala Ser Ala Thr Leu Asp Thr
    130                 135                 140

Leu Val Leu Lys Glu Asn Gln Leu Glu Val Leu Glu Val Ser Trp Leu
145                 150                 155                 160

His Gly Leu Lys Ala Leu Gly His Leu Asp Leu Ser Gly Asn Arg Leu
                165                 170                 175

Arg Lys Leu Pro Pro Gly Leu Leu Ala Asn Phe Thr Leu Leu Arg Thr
            180                 185                 190

Leu Asp Leu Gly Glu Asn Gln Leu Glu Thr Leu Pro Pro Asp Leu Leu
        195                 200                 205

Arg Gly Pro Leu Gln Leu Glu Arg Leu His Leu Glu Gly Asn Lys Leu
    210                 215                 220

Gln Val Leu Gly Lys Asp Leu Leu Pro Gln Pro Asp Leu Arg Tyr
225                 230                 235                 240

Leu Phe Leu Asn Gly Asn Lys Leu Ala Arg Val Ala Ala Gly Ala Phe
                245                 250                 255

Gln Gly Leu Arg Gln Leu Asp Met Leu Asp Leu Ser Asn Asn Ser Leu
            260                 265                 270

Ala Ser Val Pro Glu Gly Leu Trp Ala Ser Leu Gly Gln Pro Asn Trp
        275                 280                 285
```

```
Asp Met Arg Asp Gly Phe Asp Ile Ser Gly Asn Pro Trp Ile Cys Asp
        290                 295                 300

Gln Asn Leu Ser Asp Leu Tyr Arg Trp Leu Gln Ala Gln Lys Asp Lys
305                 310                 315                 320

Met Phe Ser Gln Asn Asp Thr Arg Cys Ala Gly Pro Glu Ala Val Lys
                325                 330                 335

Gly Gln Thr Leu Leu Ala Val Ala Lys Ser Gln
            340                 345

<210> SEQ ID NO 3
<211> LENGTH: 24
<212> TYPE: PRT
<213> ORGANISM: Homo sapiens

<400> SEQUENCE: 3

Leu Gln Glu Leu His Leu Ser Ser Asn Gly Leu Glu Ser Leu Ser Pro
1               5                   10                  15

Glu Phe Leu Arg Pro Val Pro Gln
            20

<210> SEQ ID NO 4
<211> LENGTH: 24
<212> TYPE: PRT
<213> ORGANISM: Homo sapiens

<400> SEQUENCE: 4

Leu Asp Met Leu Asp Leu Ser Asn Asn Ser Leu Ala Ser Val Pro Glu
1               5                   10                  15

Gly Leu Trp Ala Ser Leu Gly Gln
            20

<210> SEQ ID NO 5
<211> LENGTH: 26
<212> TYPE: PRT
<213> ORGANISM: Homo sapiens

<400> SEQUENCE: 5

Lys Met Phe Ser Gln Asn Asp Thr Arg Cys Ala Gly Pro Glu Ala Val
1               5                   10                  15

Lys Gly Gln Thr Leu Leu Ala Val Ala Lys
            20                  25

<210> SEQ ID NO 6
<211> LENGTH: 342
<212> TYPE: PRT
<213> ORGANISM: Mus musculus

<400> SEQUENCE: 6

Met Val Ser Trp Gln His Gln Gly Ser Leu Gln Asp Leu Lys Thr Cys
1               5                   10                  15

Leu Ala Arg Thr Leu Phe Leu Leu Ala Leu Leu Gly Arg Val Ser Ser
            20                  25                  30

Leu Lys Glu Cys Leu Ile Leu Gln Ser Ala Glu Gly Ser Thr Val Ser
        35                  40                  45

Cys His Gly Pro Thr Glu Phe Pro Ser Ser Leu Pro Ala Asp Thr Val
    50                  55                  60

His Leu Ser Val Glu Phe Ser Asn Leu Thr Gln Leu Pro Ala Ala Ala
65                  70                  75                  80

Leu Gln Gly Cys Pro Gly Leu Arg Glu Leu His Leu Ser Ser Asn Arg
```

-continued

```
                85                  90                  95
Leu Gln Ala Leu Ser Pro Glu Leu Leu Ala Pro Val Pro Arg Leu Arg
            100                 105                 110
Ala Leu Asp Leu Thr Arg Asn Ala Leu Arg Ser Leu Pro Pro Gly Leu
            115                 120                 125
Phe Ser Thr Ser Ala Asn Leu Ser Thr Leu Val Leu Arg Glu Asn Gln
130                 135                 140
Leu Arg Glu Val Ser Ala Gln Trp Leu Gln Gly Leu Asp Ala Leu Gly
145                 150                 155                 160
His Leu Asp Leu Ala Glu Asn Gln Leu Ser Ser Leu Pro Ser Gly Leu
                165                 170                 175
Leu Ala Ser Leu Gly Ala Leu His Thr Leu Asp Leu Gly Tyr Asn Leu
            180                 185                 190
Leu Glu Ser Leu Pro Glu Gly Leu Leu Arg Gly Pro Arg Arg Leu Gln
            195                 200                 205
Arg Leu His Leu Glu Gly Asn Arg Leu Gln Arg Leu Glu Asp Ser Leu
            210                 215                 220
Leu Ala Pro Gln Pro Phe Leu Arg Val Leu Phe Leu Asn Asp Asn Gln
225                 230                 235                 240
Leu Val Gly Val Ala Thr Gly Ser Phe Gln Gly Leu Gln His Leu Asp
                245                 250                 255
Met Leu Asp Leu Ser Asn Asn Ser Leu Ser Ser Thr Pro Pro Gly Leu
            260                 265                 270
Trp Ala Phe Leu Gly Arg Pro Thr Arg Asp Met Gln Asp Gly Phe Asp
            275                 280                 285
Ile Ser His Asn Pro Trp Ile Cys Asp Lys Asn Leu Ala Asp Leu Cys
            290                 295                 300
Arg Trp Leu Val Ala Asn Arg Asn Lys Met Phe Ser Gln Asn Asp Thr
305                 310                 315                 320
Arg Cys Ala Gly Pro Glu Ala Met Lys Gly Gln Arg Leu Leu Asp Val
                325                 330                 335
Ala Glu Leu Gly Ser Leu
            340

<210> SEQ ID NO 7
<211> LENGTH: 248
<212> TYPE: PRT
<213> ORGANISM: Mus musculus

<400> SEQUENCE: 7

His Leu Ser Ser Asn Arg Leu Gln Ala Leu Ser Pro Glu Leu Leu Ala
1               5                   10                  15
Pro Val Pro Arg Leu Arg Ala Leu Asp Leu Thr Arg Asn Ala Leu Arg
            20                  25                  30
Ser Leu Pro Pro Gly Leu Phe Ser Thr Ser Ala Asn Leu Ser Thr Leu
        35                  40                  45
Val Leu Arg Glu Asn Gln Leu Arg Glu Val Ser Ala Gln Trp Leu Gln
    50                  55                  60
Gly Leu Asp Ala Leu Gly His Leu Asp Leu Ala Glu Asn Gln Leu Ser
65                  70                  75                  80
Ser Leu Pro Ser Gly Leu Leu Ala Ser Leu Gly Ala Leu His Thr Leu
                85                  90                  95
Asp Leu Gly Tyr Asn Leu Leu Glu Ser Leu Pro Glu Gly Leu Leu Arg
            100                 105                 110
```

```
Gly Pro Arg Arg Leu Gln Arg Leu His Leu Glu Gly Asn Arg Leu Gln
            115                 120                 125

Arg Leu Glu Asp Ser Leu Leu Ala Pro Gln Pro Phe Leu Arg Val Leu
        130                 135                 140

Phe Leu Asn Asp Asn Gln Leu Val Gly Val Ala Thr Gly Ser Phe Gln
145                 150                 155                 160

Gly Leu Gln His Leu Asp Met Leu Asp Leu Ser Asn Asn Ser Leu Ser
                165                 170                 175

Ser Thr Pro Pro Gly Leu Trp Ala Phe Leu Gly Arg Pro Thr Arg Asp
                180                 185                 190

Met Gln Asp Gly Phe Asp Ile Ser His Asn Pro Trp Ile Cys Asp Lys
            195                 200                 205

Asn Leu Ala Asp Leu Cys Arg Trp Leu Val Ala Asn Arg Asn Lys Met
        210                 215                 220

Phe Ser Gln Asn Asp Thr Arg Cys Ala Gly Pro Glu Ala Met Lys Gly
225                 230                 235                 240

Gln Arg Leu Leu Asp Val Ala Glu
                245

<210> SEQ ID NO 8
<211> LENGTH: 252
<212> TYPE: PRT
<213> ORGANISM: Homo sapiens

<400> SEQUENCE: 8

Leu Gln Glu Leu His Leu Ser Ser Asn Gly Leu Glu Ser Leu Ser Pro
1               5                   10                  15

Glu Phe Leu Arg Pro Val Pro Gln Leu Arg Val Leu Asp Leu Thr Arg
            20                  25                  30

Asn Ala Leu Thr Gly Leu Pro Pro Gly Leu Phe Gln Ala Ser Ala Thr
        35                  40                  45

Leu Asp Thr Leu Val Leu Lys Glu Asn Gln Leu Glu Val Leu Glu Val
50                  55                  60

Ser Trp Leu His Gly Leu Lys Ala Leu Gly His Leu Asp Leu Ser Gly
65                  70                  75                  80

Asn Arg Leu Arg Lys Leu Pro Pro Gly Leu Leu Ala Asn Phe Thr Leu
                85                  90                  95

Leu Arg Thr Leu Asp Leu Gly Glu Asn Gln Leu Glu Thr Leu Pro Pro
            100                 105                 110

Asp Leu Leu Arg Gly Pro Leu Gln Leu Glu Arg Leu His Leu Glu Gly
        115                 120                 125

Asn Lys Leu Gln Val Leu Gly Lys Asp Leu Leu Leu Pro Gln Pro Asp
    130                 135                 140

Leu Arg Tyr Leu Phe Leu Asn Gly Asn Lys Leu Ala Arg Val Ala Ala
145                 150                 155                 160

Gly Ala Phe Gln Gly Leu Arg Gln Leu Asp Met Leu Asp Leu Ser Asn
                165                 170                 175

Asn Ser Leu Ala Ser Val Pro Glu Gly Leu Trp Ala Ser Leu Gly Gln
            180                 185                 190

Pro Asn Trp Asp Met Arg Asp Gly Phe Asp Ile Ser Gly Asn Pro Trp
        195                 200                 205

Ile Cys Asp Gln Asn Leu Ser Asp Leu Tyr Arg Trp Leu Gln Ala Gln
    210                 215                 220

Lys Asp Lys Met Phe Ser Gln Asn Asp Thr Arg Cys Ala Gly Pro Glu
225                 230                 235                 240
```

```
Ala Val Lys Gly Gln Thr Leu Leu Ala Val Ala Lys
                245                 250

<210> SEQ ID NO 9
<211> LENGTH: 252
<212> TYPE: PRT
<213> ORGANISM: Mus musculus

<400> SEQUENCE: 9

Leu Arg Glu Leu His Leu Ser Ser Asn Arg Leu Gln Ala Leu Ser Pro
  1               5                  10                  15

Glu Leu Leu Ala Pro Val Pro Arg Leu Arg Ala Leu Asp Leu Thr Arg
             20                  25                  30

Asn Ala Leu Arg Ser Leu Pro Pro Gly Leu Phe Ser Thr Ser Ala Asn
             35                  40                  45

Leu Ser Thr Leu Val Leu Arg Glu Asn Gln Leu Arg Glu Val Ser Ala
 50                  55                  60

Gln Trp Leu Gln Gly Leu Asp Ala Leu Gly His Leu Asp Leu Ala Glu
 65                  70                  75                  80

Asn Gln Leu Ser Ser Leu Pro Ser Gly Leu Leu Ala Ser Leu Gly Ala
                 85                  90                  95

Leu His Thr Leu Asp Leu Gly Tyr Asn Leu Leu Glu Ser Leu Pro Glu
            100                 105                 110

Gly Leu Leu Arg Gly Pro Arg Arg Leu Gln Arg Leu His Leu Glu Gly
            115                 120                 125

Asn Arg Leu Gln Arg Leu Glu Asp Ser Leu Leu Ala Pro Gln Pro Phe
130                 135                 140

Leu Arg Val Leu Phe Leu Asn Asp Asn Gln Leu Val Gly Val Ala Thr
145                 150                 155                 160

Gly Ser Phe Gln Gly Leu Gln His Leu Asp Met Leu Asp Leu Ser Asn
                165                 170                 175

Asn Ser Leu Ser Ser Thr Pro Pro Gly Leu Trp Ala Phe Leu Gly Arg
            180                 185                 190

Pro Thr Arg Asp Met Gln Asp Gly Phe Asp Ile Ser His Asn Pro Trp
            195                 200                 205

Ile Cys Asp Lys Asn Leu Ala Asp Leu Cys Arg Trp Leu Val Ala Asn
            210                 215                 220

Arg Asn Lys Met Phe Ser Gln Asn Asp Thr Arg Cys Ala Gly Pro Glu
225                 230                 235                 240

Ala Met Lys Gly Gln Arg Leu Leu Asp Val Ala Glu
                245                 250
```

TREATMENT OF VASCULOPROLIFERATIVE CONDITIONS WITH LRG1 ANTAGONISTS

CROSS-REFERENCE TO RELATED APPLICATIONS

This application is a Divisional of U.S. patent application Ser. No. 13/393,531 filed on May 11, 2012, currently pending, which is a U.S. National Phase Patent Application of International Application No. PCT/GB2010/001681, filed Sep. 6, 2010, which claims priority to and the benefit of United Kingdom Patent Application No. 0915515.1, filed on Sep. 4, 2009, the entire contents of each of which are incorporated herein by reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 251502010310SeqList.txt, date recorded: Jun. 18, 2014, size: 15,757 bytes).

FIELD OF THE INVENTION

The invention is in the field of molecular physiology and relates to the use of antagonists of Leucine-rich alpha-2-glycoprotein 1 (Lrg1) for use in the treatment or prevention of vasculoproliferative conditions, particularly in the eye and in the treatment of tumours that exhibit vascular proliferation.

BACKGROUND OF THE INVENTION

Aberrant remodelling of the retinal vasculature is a prominent feature of sight-threatening conditions such as diabetic retinopathy, retinal vein occlusion, retinopathy of prematurity, age-related macular degeneration and macular telangiectasia. These vascular changes manifest themselves as both new capillary growth from pre-existing retinal vessels (angiogenesis) and the development of vascular malformations of existing vessels (e.g., telangiectasia). This pathogenic vascular remodelling in these diseases is a major contributing factor to loss of vision.

Similar vascular pathology and dysfunction also accompanies tumour growth, where angiogenesis permits the enlargement and growth of solid tumours.

Substantial resource has been directed towards gaining an understanding of the mechanisms that drive these vascular responses (referred to as angiogenesis, neoangiogenesis, vascular proliferation, vascular remodelling, vascular pathology). Of the various molecules identified as playing an important role in the process, the vascular endothelial growth factors (VEGFs) and their receptors are viewed as critical components. Therapeutic targeting of the VEGF pathway in ocular angiogenesis using the anti-cancer agent Avastin® (or the closely related Lucentis) has resulted in improved clinical outcome, at least over the short term, of a number of sight-threatening conditions. However, there is concern over the long-term use of anti-VEGF strategies for the treatment of retinal vascular problems as VEGF has both neuroprotective activities and housekeeping roles such as the maintenance of choroidal fenestration. Moreover, although VEGF is considered to be the principal pro-angiogenic factor in neoangiogenesis, the process requires coordinated crosstalk between many factors, and the biological basis for other vascular changes, such as the formation of dilated and tortuous telangiectatic vessels, is not known.

There is therefore a need to identify alternative therapeutic targets and novel drugs which, in isolation or in combination with existing therapies, may be more effective and possess fewer off-target effects for the treatment of conditions where uncontrolled blood vessel growth and/or remodelling contributes to the disease.

SUMMARY OF THE INVENTION

We have identified Leucine-rich alpha-2-glycoprotein 1 (Lrg1 gene identifiers: HGNC: 29480; Entrez Gene: 116844; Ensembl: ENSG00000171236; UniProtKB: P02750) as a drugable target for the modulation of pathogenic vascular remodelling.

Lrg1 was identified in 1977 (Haupt & Baudner, 1977) and its primary structure determined in 1985 (Takahashi et al, 1985). Lrg1 is highly evolutionarily conserved between mice and humans, polyclonal antibodies to human Lrg1 are commercially available and there are reports of concomitant increases in the level of transforming growth factor beta 1 (TGFβ1), TGFβ receptor II (TGFβRII) and Lrg1 in certain diseases (Sun et al, 1995; Li et al, 1997). Other groups have identified Lrg1 as a biomarker of certain diseases (US 2005/0064516; WO 2008/092214) and as a ligand for cytochrome c (US 2007/0184503). Dysfunction of TGFβ signalling in endothelial cells leads to the disease hemorrhagic hereditary telangiectasia (HHT).

In this group of diseases, which are characterised by vascular abnormalities including telangiectases, mutations in the TGFβ endothelial accessory receptor endoglin and the TβRI co-receptor ALKβ lead to HHT1 (McAllister et al. 1994) and HHT2 (Johnson et al. 1995) respectively. TGFβ has also been found to be increased in the retina of patients with diabetic retinopathy (Spirin et al., 1999) where vascular remodelling is prevalent. Lrg1 expression has also been found to be increased in the plasma of certain tumour patients, suggesting that it may serve as a possible tumour biomarker (Heo et al, 2007; Ferrero et al, 2009; Kakisaka et al, 2007). However, very little is known about the biology of Lrg1.

We have now identified Lrg1 as a drugable target for the modulation of pathogenic vascular remodelling, particularly in the eye and in tumours that exhibit vasculoproliferation.

Using mouse models of retinal disease involving vascular changes, we first determined that, amongst other genes, Lrg1 is upregulated in the vessels of these diseased retinas. Increased expression of Lrg1 in the retina of these mouse models was then validated by quantitative PCR and western blotting and its retinal distribution confirmed as vascular by in situ hybridisation and immunohistochemistry. These models are standard models of angiogenesis and are applicable to angiogenesis at sites other than the eye.

We then investigated the connection between Lrg1 and the TGFβ signalling pathway.

In endothelial cells TGFβ signaling can occur through TGFβ receptor II associating either with the ubiquitous TGFβ type I receptor activin receptor-like kinase 5 (ALK5) or the endothelial cell specific ALK1 with the cellular response depending on which pathway predominates. In the case of ALK5 there is under certain conditions increased ECM deposition and cell quiescence whilst with ALK1 there is endothelial cell activation manifest as increased migration and proliferation. This differential signalling is partly controlled by the concentration/bioavailability of TGFβ and by members of a family of downstream effector proteins called Smads, whereby Smad 2 and 3 are activated by ALK5 and Smad 1, 5 and 8 by ALK1.

Immunoprecipitation showed that Lrg1 associates with both TGFβRII and ALK1, suggesting that Lrg1 has a role in connection with these two molecules as part of the TGFβ signalling complex.

We hypothesised, therefore, that Lrg1 acts as a modulator of TGFβ signalling, causing fine-tuning between the ALK1- and ALK5-activated signalling cascades. In support of this, Lrg1 knockdown in endothelial cells with siRNA blocks TGFβ-mediated increased cell proliferation and reduced Smad5 phosphorylation whilst Lrg1 overexpression leads to an enhanced proliferation, downregulation in Smad2 expression and increased Smad5 phosphorylation. These observations therefore reveal one way in which Lrg1 may regulate angiogenesis. Also, in a Matrigel™ angiogenesis assay to investigate the effect of Lrg1 on "vessel" formation, the degree of vascular formation, as measured by vessel formation, tube formation and cord formation was significantly increased when conditioned medium from Lrg1 overexpressing cells was added and the increased vascularisation correlated with Lrg1 protein expression in the medium.

These data are consistent with decreased signalling via the TGFβRII/ALK5 receptor complex pathway and hence a shift towards activation of the vasculopathogenic TGFβRII/ALK1 signalling pathway.

This suggests that blocking Lrg1 within the TGFβ signalling complex has the potential to divert TGFβ away from pathogenic vascularisation. To test this proposition, we determined whether we could block endothelial Smad5 phosphorylation induced by TGFβ with either an anti-Lrg1 antibody or by peptide sequences derived from Lrg1 that could be expected to compete with Lrg1 for binding to ALK1. The anti-Lrg1 antibody caused reduction in phosphorylation whilst one of the peptides exhibited a particularly large reduction in phosphorylation.

Therefore, Smad5 phosphorylation can be inhibited by blocking Lrg1 and, because Smad5 is associated with the vasculopathogenic ALK1-activated signalling cascade, this demonstrates that blocking Lrg1 has the potential to block that cascade relative to the non-pathogenic, ALK5-activated alternative cascade.

Taken together, these data suggest that: (a) Lrg1 interacts with both TGFβRII and ALK1, promoting directly or through one or more intermediaries the interaction between TGFβRII and ALK1 as opposed to ALK5, such that (b) blocking Lrg1 will direct the activity of TGFβ away from the vasculopathogenic, ALK1-activated signalling cascade and into the non-pathogenic, ALK5-activated cascade, with the result that (c) Lrg1 is a valid drug target for the treatment of pathogenic vascularisation in the eye and elsewhere. Treatments with various Lrg1-blocking agents, notably peptide fragments of Lrg1, monoclonal antibodies to Lrg1 and siRNA molecules, can hence be envisaged for ocular and other disorders that involve pathogenic tissue vascularisation. Without being bound by theory, FIG. 16 illustrates the role for Lrg1 that is suggested by our data.

Additionally, our data suggest that, in contrast to VEGF, Lrg1 may be involved only in pathogenic vascularisation in the eye and not in normal developmental vascularisation or vascular homeostasis. This makes it a potentially superior target to VEGF in terms of avoiding interference with processes that it is not desirable to disrupt. A further attraction of Lrg1 as a target is that it is extracellular and hence more easily accessed via systemic therapeutic routes.

Experiments were also conducted to investigate the role of Lrg1 ex vivo and in vivo. Our experiments show that angiogenic vessel sprouting is reduced in aortic rings from Lrg1 knockout mice as compared to aortic rings from control mice. Also, we found that choroidal neovascularisation (CNV) after retinal injury and retinal neovascularisation following oxygen-induced retinopathy (OIR) was reduced in Lrg1 knockout mice as compared to control mice.

As evidence of the role of Lrg1 in human pathology, our data shows that Lrg1 and TGFβ expression are increased in human patients suffering from proliferative diabetic retinopathy, supporting the in vivo data obtained from mice.

We have also demonstrated that antibodies against Lrg1 are capable of inhibiting tube formation by human umbilical vein endothelial cells (HUVEC) in Matrigel™ angiogenesis assays. These data suggest that antibodies against Lrg1 will be useful in the treatment or prevention of vasculoproliferative conditions, particularly those of the eye and of tumours that exhibit vasculoproliferation.

Accordingly, the invention provides an antagonist of Leucine-rich alpha-2-glycoprotein 1 (Lrg1) for use in the treatment or prevention of a vasculoproliferative condition.

The invention also provides a method of identifying antagonists of Lrg1 comprising: providing a candidate antagonist, and determining whether or not said candidate antagonist blocks function or activity of Lrg1; wherein said candidate antagonist is identified as an antagonist of Lrg1 if blocking of the function or activity Lrg1 is observed.

The invention also provides a monoclonal antibody which specifically recognises an epitope within amino acids L1-24 of Appendix 2 or L94-117 of Appendix 3 (SEQ ID NO:3), L169-192 of Appendix 2 or L262-285 of Appendix 3 (SEQ ID NO:4) or L227-252 of Appendix 2 or L320-345 of Appendix 3 (SEQ ID NO:5) and blocks the activity of Lrg1.

The invention also provides a monoclonal antibody which specifically recognises an epitope within amino acids L1-24 of Appendix 2 or L94-117 of Appendix 3 (SEQ ID NO:3), L169-192 of Appendix 2 or L262-285 of Appendix 3 (SEQ ID NO:4) or L227-252 of Appendix 2 or L320-345 of Appendix 3 (SEQ ID NO:5) and blocks the interaction between ALK1, TGFβRII and/or TGFβ and Lrg1.

The invention also provides a method for producing such an antibody, comprising: immunising a non-human mammal with an immunogen comprising an epitope within the sequence of L1-24 of Appendix 2 or L94-117 of Appendix 3 (SEQ ID NO:3), L169-192 of Appendix 2 or L262-285 of Appendix 3 (SEQ ID NO:4) or L227-252 of Appendix 2 or L320-345 of Appendix 3 (SEQ ID NO:5) of Lrg1; and obtaining an antibody preparation from said mammal and deriving therefrom monoclonal antibodies that specifically recognise said epitope.

The invention also provides a method for determining what sites within Lrg1 can be targeted to block the function or activity of Lrg1, comprising providing peptide fragments of the Lrg1 protein; and determining whether or not said each of said peptide fragments blocks the function or activity of Lrg1.

The invention also provides use of an antagonist of Lrg1 in the manufacture of a medicament for the treatment or prevention of a vasculoproliferative condition.

The invention also provides a method of treating a vasculoproliferative condition comprising administering to a patient in need thereof an effective amount of an antagonist of Lrg1.

FIG. 2. A. Schematic representation of Lrg1 protein and its proposed glycosylation sites. B. Structure of Lrg1 protein predicted by ROBETTA (University of Washington, USA).

Figure 3:
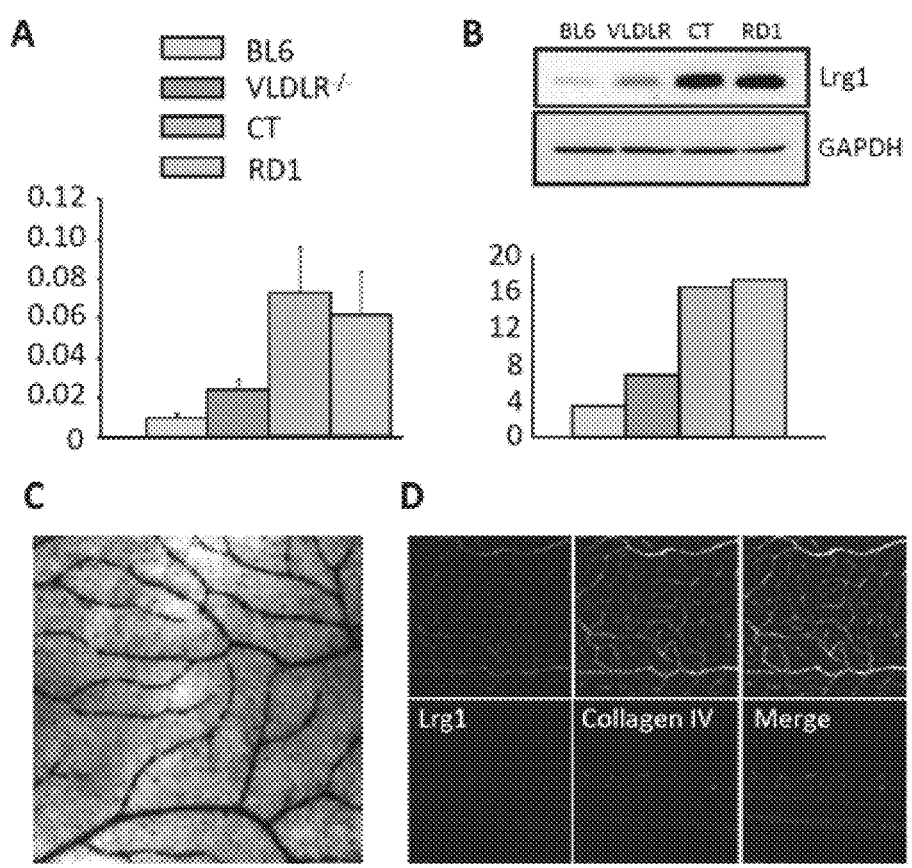

FIG. 3. A. Quantitative RT PCR analysis of Lrg1 expression in whole mouse retina of C57B16 control mice (BL6), VLDL receptor KO mice (VLDLR$^{-/-}$), Curlytail-J mice (CT) and the retinal dystrophy 1 mice (RD1). B. Western blot of Lrg1 protein expression (top) and semi-quantitation (bottom) from whole retina. C. In situ hybridisation of normal retina showing Lrg1 gene expression. D. Immunohistochemical staining of Lrg1 in retinal flat mounts (top) and retinal sections (bottom) showing vascular pattern of expression.

FIG. 4. A. Co-immunoprecipitation from GPNT endothelial cell lysates of Lrg1 with TGFβRII and ALK1. B. Recombinant HA-tagged Lrg1 associates with both TGFβ and TGFβRII. C. Co-localisation of Lrg1 and TGFβRII expression in GPNT endothelial cells. D. Endothelial cell proliferation assay demonstrating that Lrg1 knockdown attenuates TGFβ induced proliferation and decreased Smad1/5 phosphorylation (*p<0.05). E. Endothelial cell proliferation assay demonstrating that overexpression of Lrg1 enhances TGFβ induced proliferation and increases Smad1/5 phosphorylation (*p<0.05).

Figure 5:
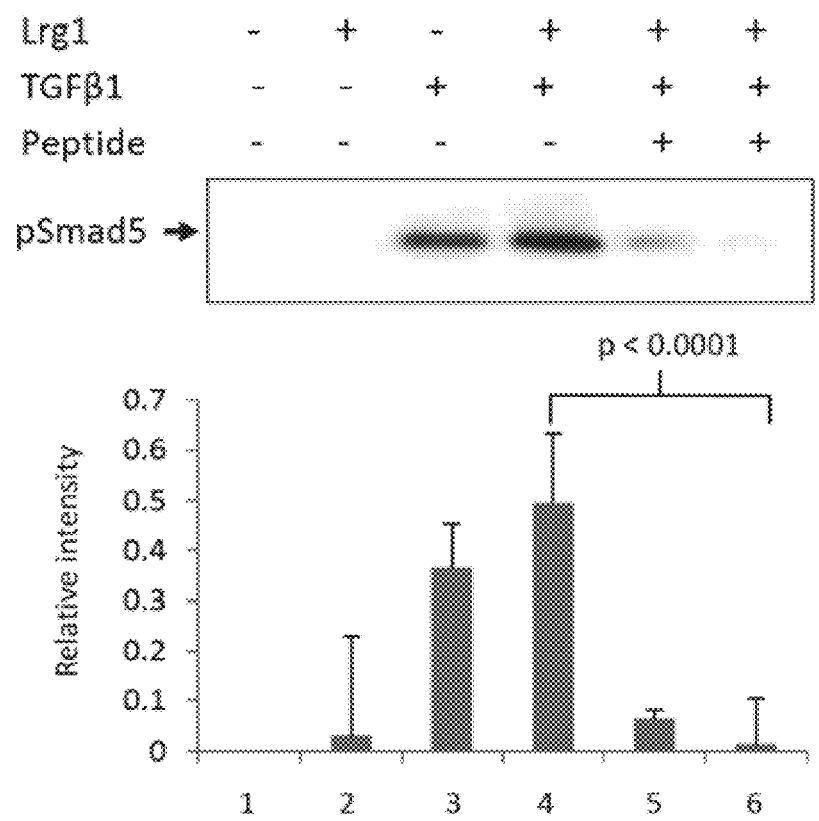

FIG. 5. Lrg1 blocking peptide derived from the C-terminus inhibits Lrg1/TGFβ1 induced Smad5 phosphorylation in GPNT endothelial cells (n=3 for each condition, p<0.0001). The two right hand lanes are the C-terminal peptide alone, and the three peptides L1-24 of Appendix 2 or L94-117 of Appendix 3 (SEQ ID NO:3), L169-192 of Appendix 2 or L262-285 of Appendix 3 (SEQ ID NO:4) or L227-252 of Appendix 2 or L320-345 of Appendix 3 (SEQ ID NO:5) combined.

Figure 6:
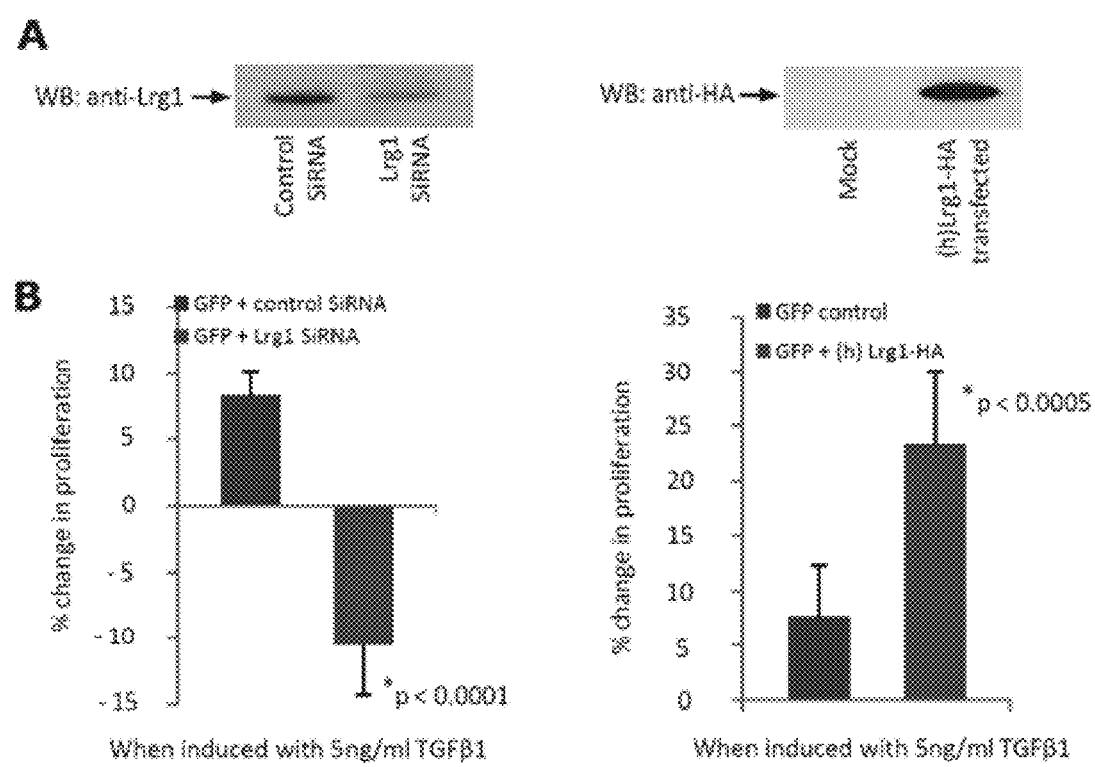

FIG. 6. A. Western blot of Lrg1 knockdown in GPNT endothelial cells with siRNA and Lrg1 over-expression in GPNT cells. B. Lrg1 knockdown reduces TGFβ1-mediated endothelial cell proliferation (*p<0.0001) and Lrg1 over-expression enhances TGFβ1-mediated endothelial cell proliferation (*p<0.0005) (n=3 for each condition).

Figure 7:
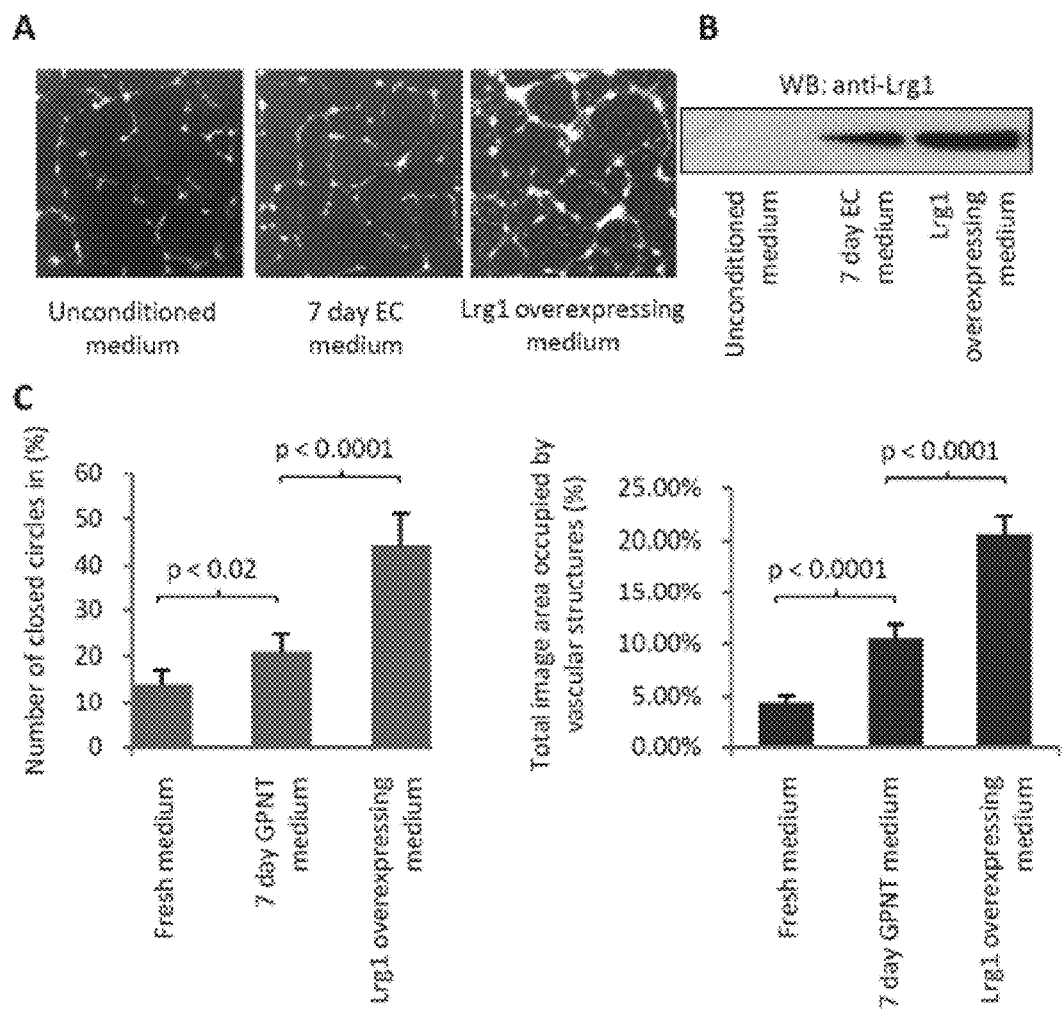

FIG. 7. Effect of Lrg1 on HUVEC "vessel" formation in vitro. A. Untreated media or media from control endothelial cell (EC) or from EC overexpressing Lrg1 was added to a Matrigel™ angiogenesis assay. Lrg1 conditioned medium enhanced HUVEC "cord" formation. B. Western blot of Lrg1 in unconditioned media, GPNT endothelial cell conditioned media (7 days) and conditioned media from GPNT cells over-expressing Lrg1. C. Quantification of Matrigel™ endothelial cord formation complexity (number of closed vascular circles and total vascular area) following different treatments (n=3 for each condition). Lrg1 conditioned media from Lrg1 overexpressing cells induced the greatest angiogenic vascular plexus as measured by number of closed vascular circles or total vascular area (p<0.0001).

Figure 8:
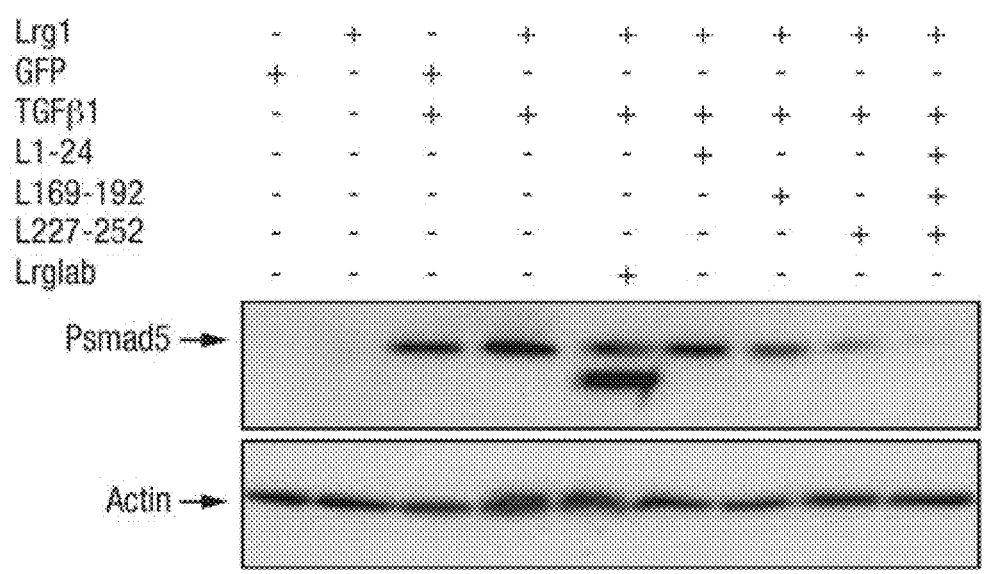

FIG. 8. Effect of Lrg1 antibody (a commercially available polyclonal antibody to the N-terminal domain of Lrg1) and Lrg1 peptides on endothelial Smad5 phosphorylation following treatment with TGFβ and Lrg1.

Figure 9:
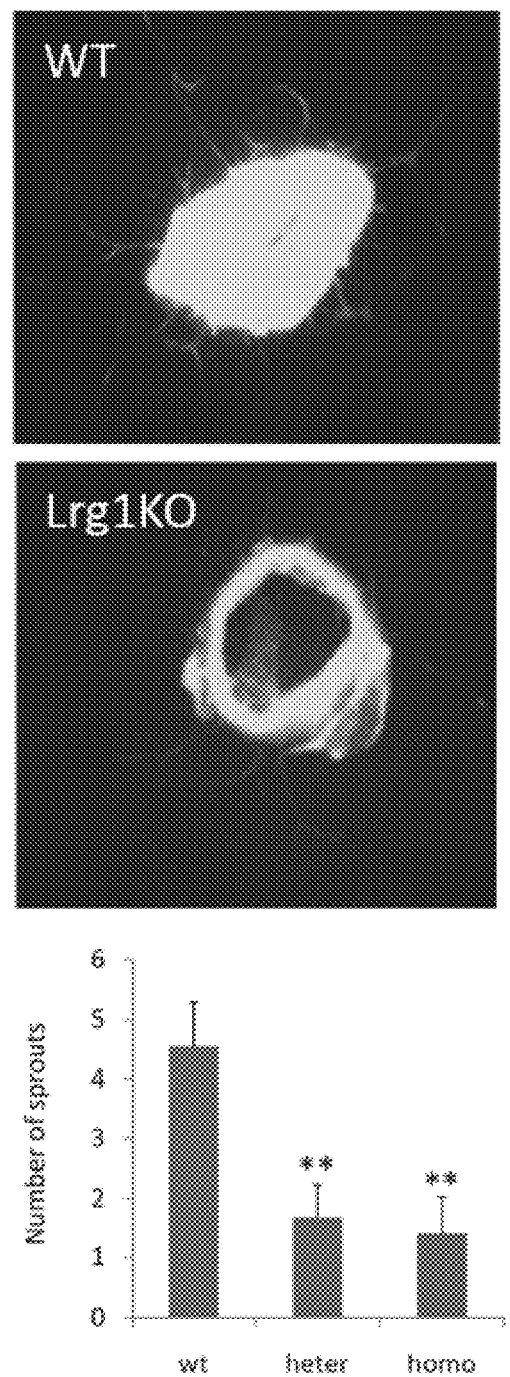

FIG. 9. Aortic rings from Lrg1 knockout mice display reduced angiogenic vessel sprouting as compared to aortic rings from wild type mice. Representative images of aortic ring angiogenesis (stained green with isolectin B4) demonstrating reduced angiogenic vessel sprouting in aortas from Lrg1 KO mice and their quantification. n=30 aortic rings for each group (**p<0.01).

Figure 10:
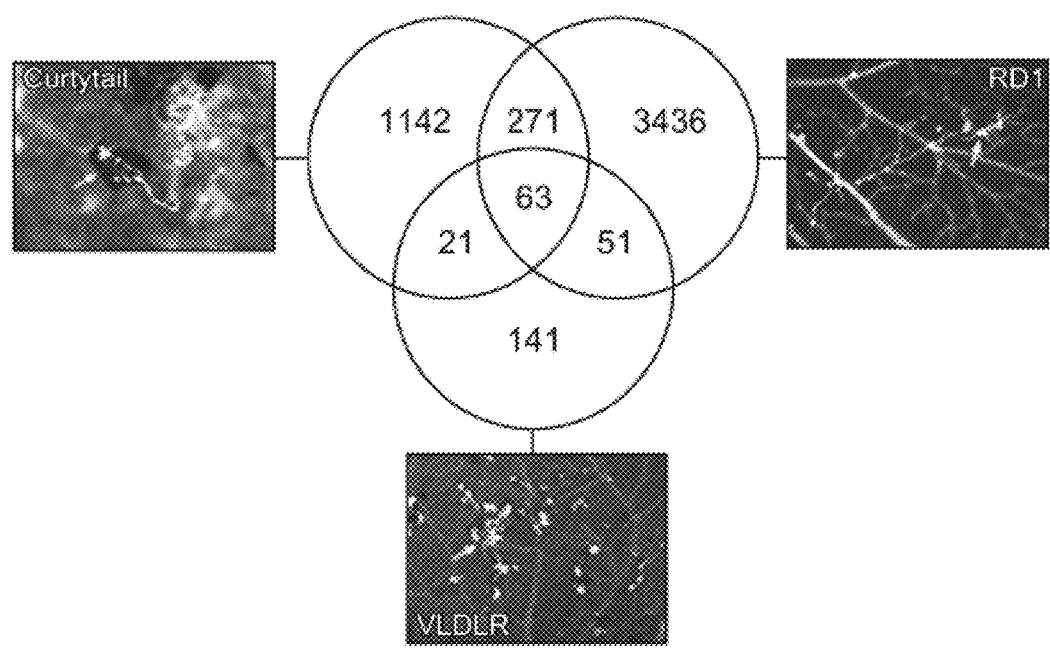

FIG. 10. Genes up-regulated in Curlytail-J, RD1 and VLDLR −/− mouse models of retinal disease.

Figure 11:
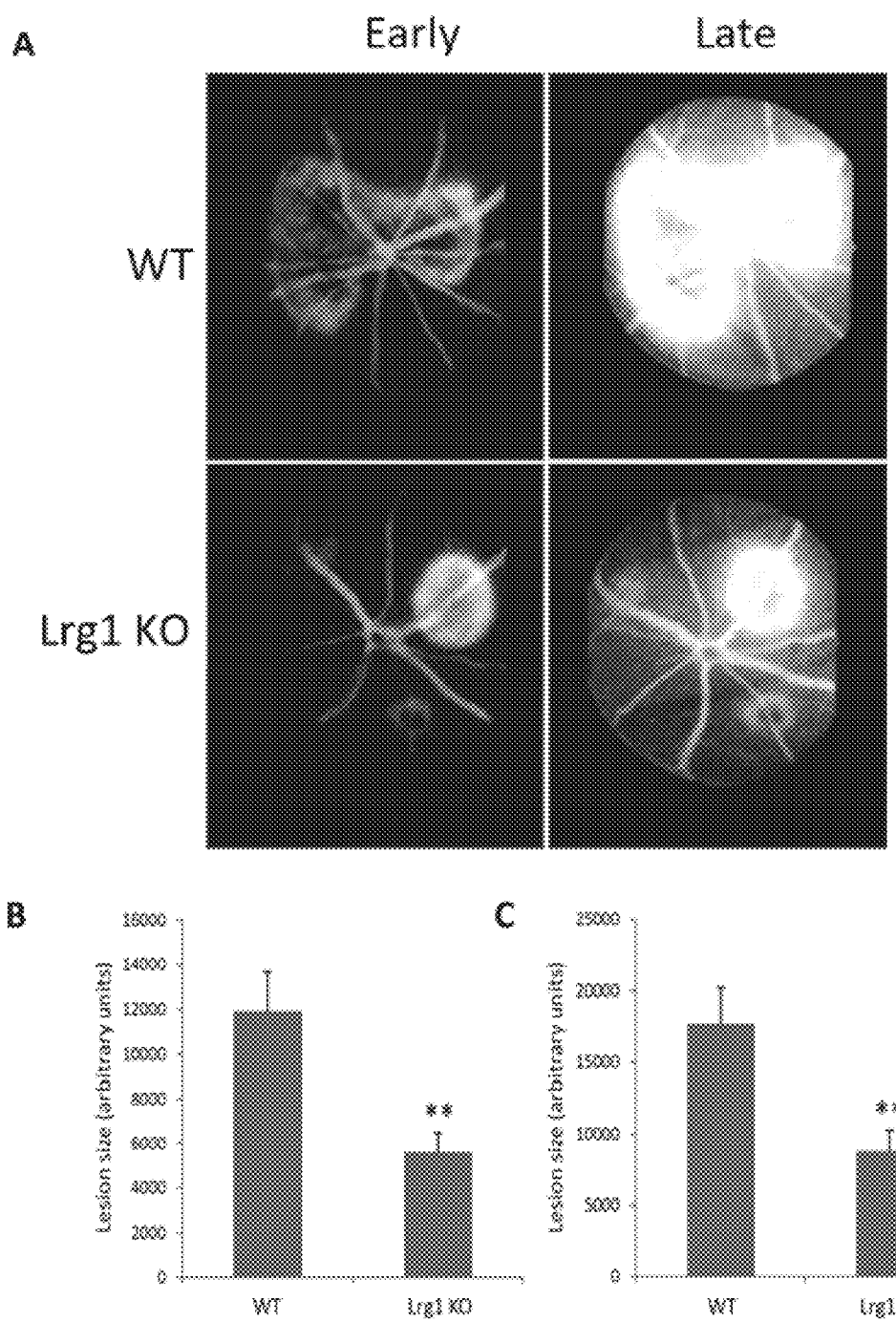

FIG. 11. A. Fluorescein angiograms (FA) of choroidal neovascularisation induced by laser burns to the retina of WT and Lrg1 KO mice. Quantitation of early (B) and late (C) FA showing size of angiogenic growth and leakage respectively recorded at 7 days post lesion. n=10 (**p<0.01).

Figure 12:
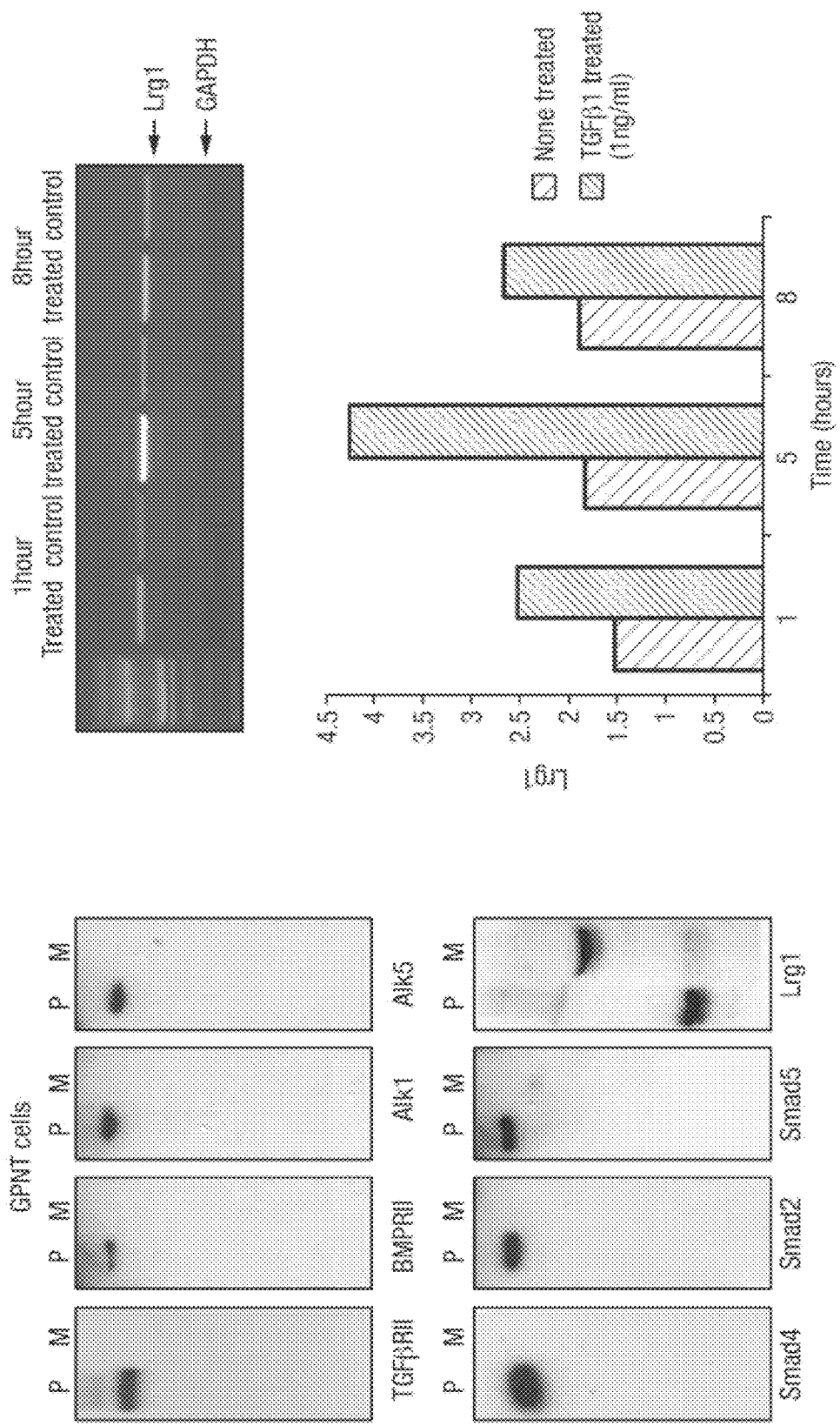

FIG. 12. (Left) The brain endothelial cell line GPNT expresses the requisite components for studying the effect of Lrg1 on TGFβ signalling. P=cell pellet; M=cell media. (Right) TGFβ induces Lrg1 gene expression in GPNT cells.

Figure 13:
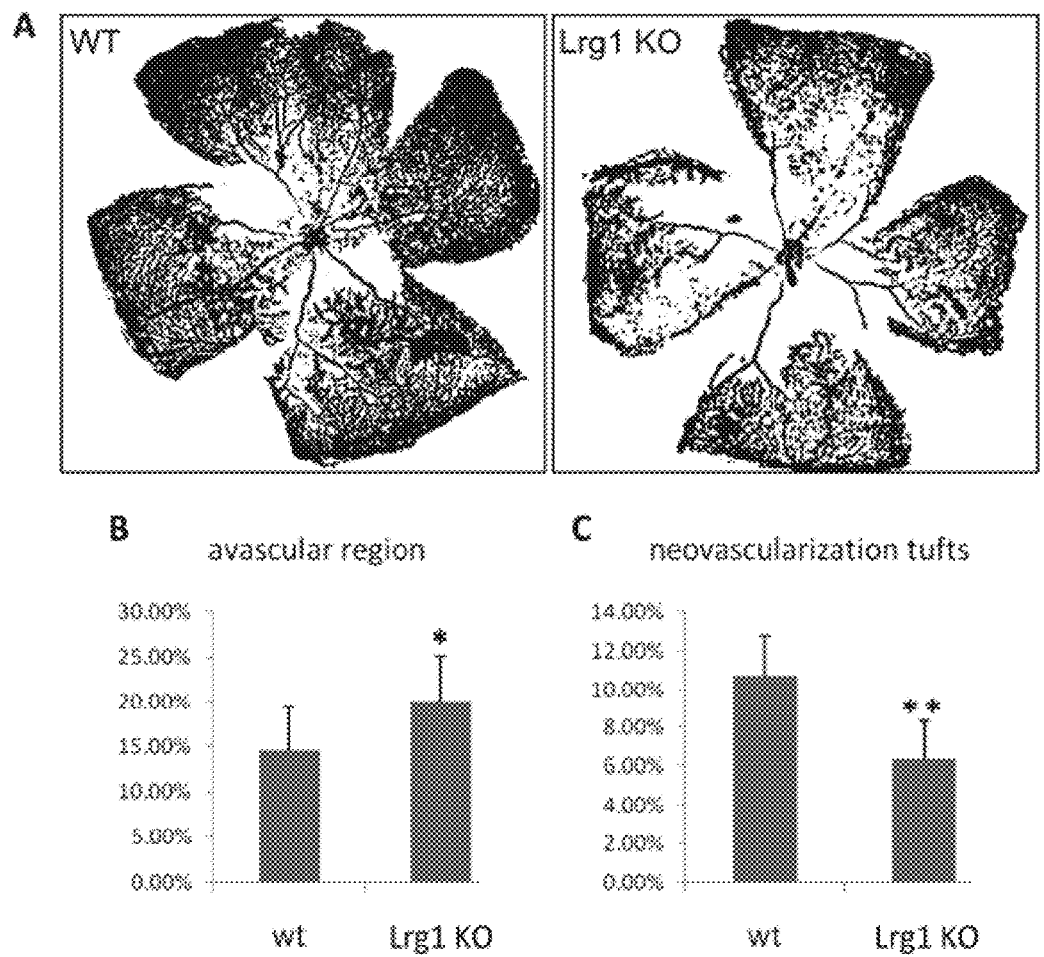

FIG. 13. Representative images of mouse retinal vasculature (stained red with isolectin B4) at P17 following oxygen-induced retinopathy (OIR) demonstrating increased avascular region and decreased neovascular tufts in Lrg1 KO mice. Quantification of (B) avascular region and (C) neovascular tufts in WT and Lrg1 KO mice (n=6 and 9 respectively). The avascular region is increased in the Lrg1 knockout (*p<0.05), with fewer neovascular tufts visible in the knockout compared with the wild type (**p0.01).

Figure 14:
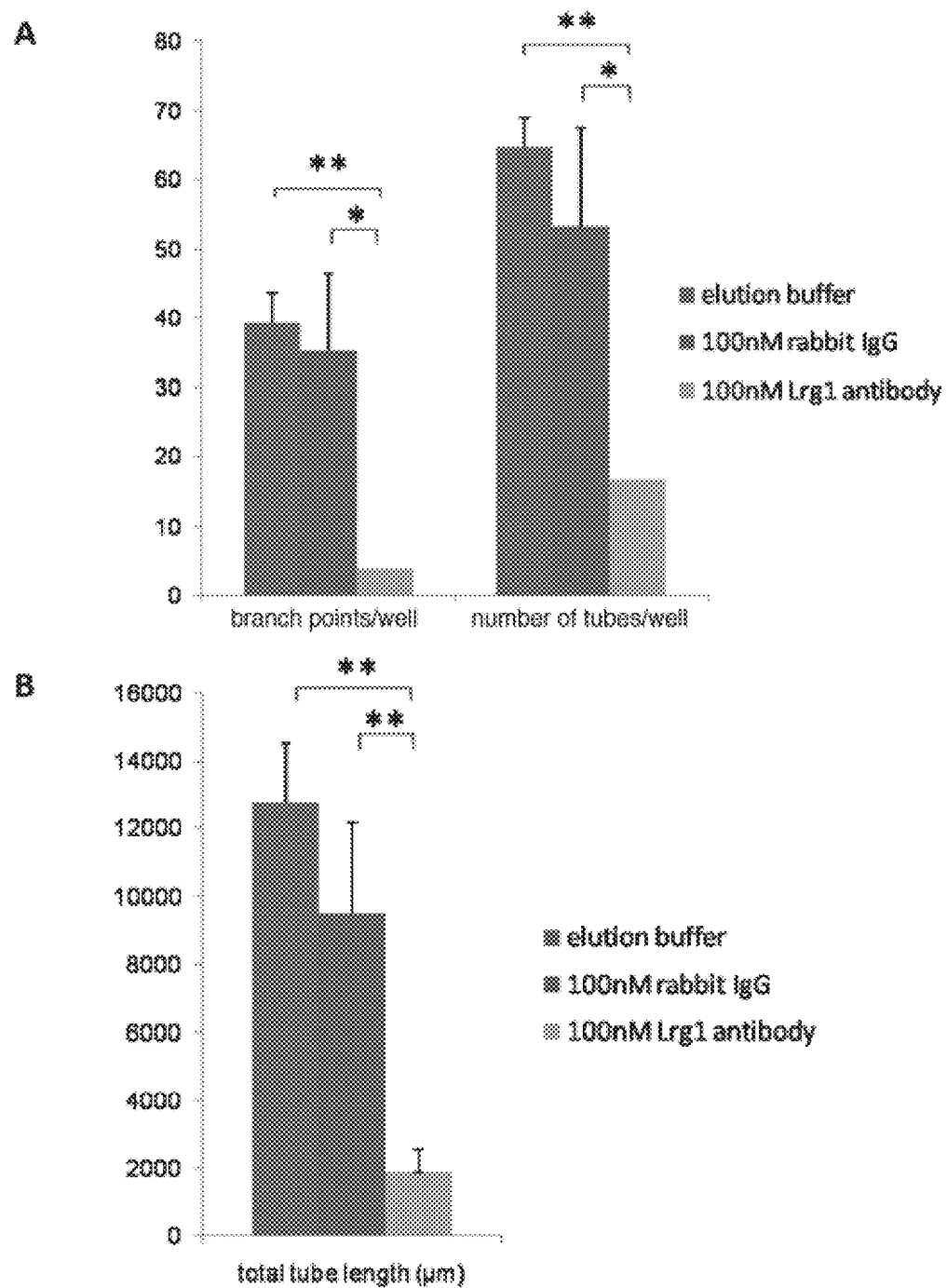

FIG. 14. Tube formation of Human Umbilical Vein Endothelial Cells (HUVEC) in Matrigel™ in vitro was reduced following addition of a neutralizing anti-human Lrg1 polyclonal antibody compared to irrelevant IgG. Tube formation was measured with regard to A. the number of branch points, tube number and B. total tube length (n=3, *p<0.05, **p<0.01).

Figure 15:
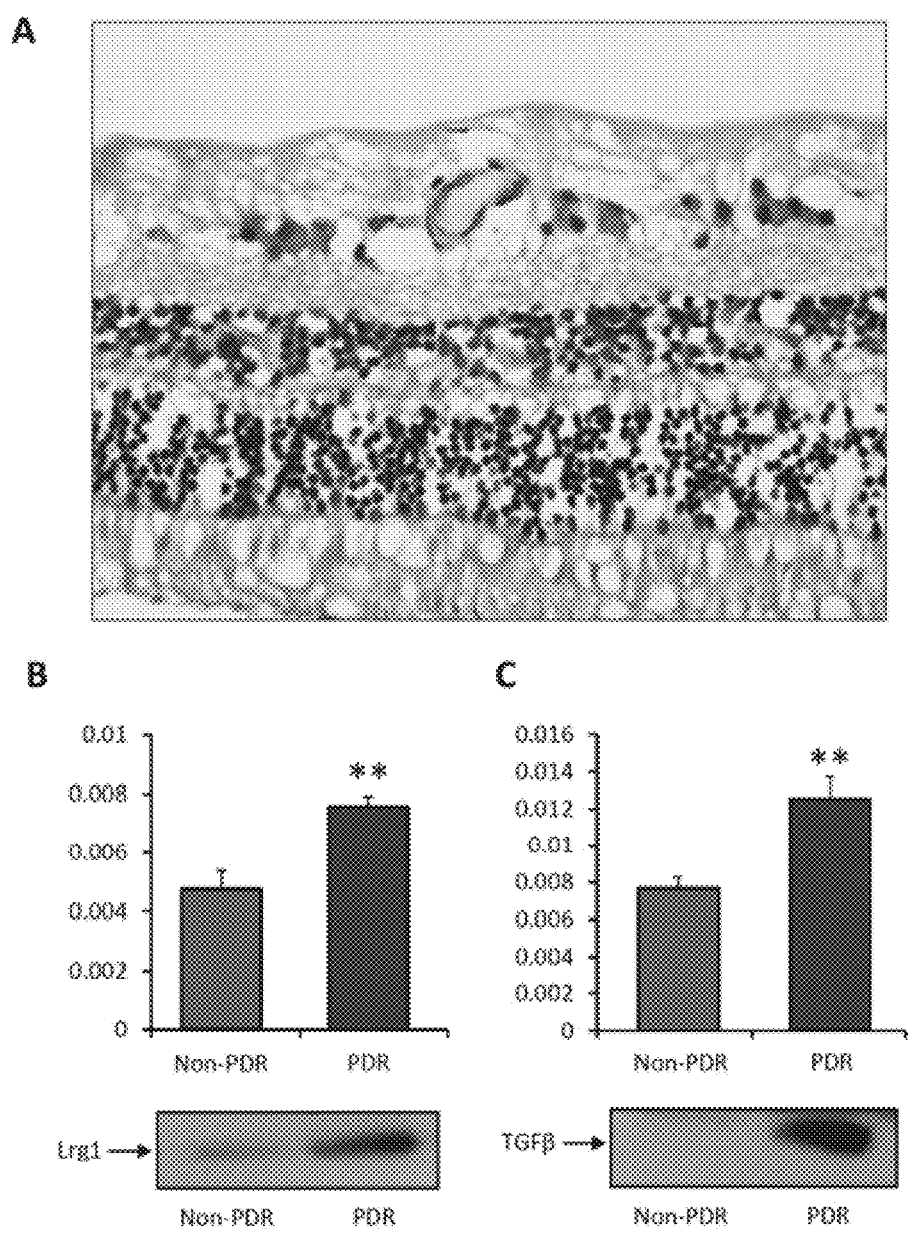

FIG. 15. A. Cross section through a human retina stained for Lrg1. B. Western blot and quantification of Lrg1 (n=4) in vitreous samples from non-diabetic patients and patients with proliferative diabetic retinopathy (PDR). C. Western blot and quantification of TGFβ1 in vitreous samples from non-diabetic patients and patients with PDR (**p<0.01).

FIG. 16. Schematic of working hypothesis. A. Under normal conditions TGFβ1 signalling is directed predominantly towards the TGFβRII/ALK5/Smad2/3 pathway and Lrg1 is sequestered in the basal lamina. B. Under pathogenic conditions increased Lrg1 expression results in a redirection of TGFβ1 signalling towards the TGFβRII/ALK1/Smad1/5/8 pathway which contributes to vascular remodelling.

DETAILED DESCRIPTION OF THE INVENTION

Blocking Lrg1

Antagonists of the invention block the function of Lrg1. Blocking of Lrg1 encompasses any reduction in its activity or function that results in reduced vasculoproliferative effects, including endothelial cell proliferation, pericyte drop-out, endothelial cell death, vascular remodelling, angiogenesis, telangiectasia, vascular leakage.

For example, blocking of Lrg1 may be via blocking its interaction with ALK1, TGFβRII and/or TGFβ, which our data suggest promotes the interaction between TGFβRII and ALK5 rather than ALK1, thus diverting the activity of TGFβ into the less-pathogenic ALK-5 activated signally cascade and away from the vasculopathogenic ALK-1 associated cascade. Blocking of Lrg1 may also result in reduced bioavailability of TGFβ.

Blocking encompasses both total and partial reduction of Lrg1 activity or function, for example total or partial prevention of the ALK1-Lrg1, TGFβRII-Lrg1 and/or TGFβ-Lrg1 interactions. For example, a blocking antagonist of the invention may reduce the activity of Lrg1 by from 10 to 50%, at least 50% or at least 70%, 80%, 90%, 95% or 99%.

Blocking of Lrg1 activity or function can be measured by any suitable means. For example, blocking of the ALK1-Lrg1, TGFβRII-Lrg1 and/or TGFβ-Lrg1 interaction can be determined by measuring the effect on Smad5 phosphorylation, on the basis that Smad5 phosphorylation is characteristic of the ALK1 activated pathway rather than the ALK5-activated one.

Blocking of Lrg1 can also be measured via assays that measure angiogenesis, for example in vitro assays such as vessel growth in Matrigel™, vessel growth from aortic rings and in vivo assays such as those that measure retinal angiogenesis (e.g., laser induced choroidal neovascularisation, oxygen-induced retinopathy).

Blocking may take place via any suitable mechanism, depending for example on the nature (see below) of the antagonist used, e.g., steric interference in any direct or indirect ALK1-Lrg1, TGFβRII-Lrg1 and/or TGFβ-Lrg1 interaction or knockdown of Lrg1 expression.

Antagonists of Lrg1

Any suitable antagonist may be used according to the invention, for example peptides and peptidomimetics, antibodies, small molecule inhibitors, double-stranded RNA, aptamers and ribozymes. Preferred antagonists include peptide fragments of Lrg1, double-stranded RNA, aptamers and antibodies.

Peptides

Peptide antagonists will typically be fragments of Lrg1 that compete with full-length Lrg1 for binding to TGFβRII and/or ALK1 and hence antagonise Lrg1. Such peptides may be linear or cyclic. Peptide antagonists will typically be from 5 to 50, preferably 10-40, 10-30 or 15-25 amino acids in length and will generally be identical to contiguous sequences from within Lrg1 but may have less than 100% identity, for example 95% or more, 90% or more or 80% or more, as long as they retain Lrg1-blocking properties. Blocking peptides can be identified in any suitable manner, for example, by systematic screening of contiguous or overlapping peptides spanning part or all of the Lrg1 sequence. Peptidomimetics may also be designed to mimic such blocking peptides.

Double-Stranded RNA

Using known techniques and based on a knowledge of the sequence of Lrg1, double-stranded RNA (dsRNA) molecules can be designed to antagonise Lrg1 by sequence homology-based targeting of Lrg1 RNA. Such dsRNAs will typically be small interfering RNAs (siRNAs), usually in a stem-loop ("hairpin") configuration, or micro-RNAs (miRNAs). The sequence of such dsRNAs will comprise a portion that corresponds with that of a portion of the mRNA encoding Lrg1. This portion will usually be 100% complementary to the target portion within the Lrg1 mRNA but lower levels of complementarity (e.g., 90% or more or 95% or more) may also be used.

Aptamers

Aptamers are generally nucleic acid molecules that bind a specific target molecule. Aptamers can be engineered completely in vitro, are readily produced by chemical synthesis, possess desirable storage properties, and elicit little or no immunogenicity in therapeutic applications. These characteristics make them particularly useful in pharmaceutical and therapeutic utilities.

As used herein, "aptamer" refers in general to a single or double stranded oligonucleotide or a mixture of such oligonucleotides, wherein the oligonucleotide or mixture is capable of binding specifically to a target. Oligonucleotide aptamers will be discussed here, but the skilled reader will appreciate that other aptamers having equivalent binding characteristics can also be used, such as peptide aptamers.

In general, aptamers may comprise oligonucleotides that are at least 5, at least 10 or at least 15 nucleotides in length. Aptamers may comprise sequences that are up to 40, up to 60 or up to 100 or more nucleotides in length. For example, aptamers may be from 5 to 100 nucleotides, from 10 to 40 nucleotides, or from 15 to 40 nucleotides in length. Where possible, aptamers of shorter length are preferred as these will often lead to less interference by other molecules or materials.

Non-modified aptamers are cleared rapidly from the bloodstream, with a half-life of minutes to hours, mainly due to nuclease degradation and clearance from the body by the kidneys. Such non-modified aptamers have utility in, for example, the treatment of transient conditions such as in stimulating blood clotting. Alternatively, aptamers may be modified to improve their half-life. Several such modifications are available, such as the addition of 2'-fluorine-substituted pyrimidines or polyethylene glycol (PEG) linkages.

Aptamers may be generated using routine methods such as the Systematic Evolution of Ligands by Exponential enrichment (SELEX) procedure. SELEX is a method for the in vitro evolution of nucleic acid molecules with highly specific binding to target molecules. It is described in, for example, U.S. Pat. Nos. 5,654,151, 5,503,978, 5,567,588 and WO 96/38579.

The SELEX method involves the selection of nucleic acid aptamers and in particular single stranded nucleic acids capable of binding to a desired target, from a collection of oligonucleotides. A collection of single-stranded nucleic acids (e.g., DNA, RNA, or variants thereof) is contacted with a target, under conditions favourable for binding, those nucleic acids which are bound to targets in the mixture are separated from those which do not bind, the nucleic acid-target complexes are dissociated, those nucleic acids which had bound to the target are amplified to yield a collection or library which is enriched in nucleic acids having the desired binding activity, and then this series of steps is repeated as necessary to produce a library of nucleic acids (aptamers) having specific binding affinity for the relevant target.

Antibodies

The term "antibody" as referred to herein includes whole antibodies and any antigen binding fragment (i.e., "antigen-binding portion") or single chains thereof. An antibody refers to a glycoprotein comprising at least two heavy (H) chains and two light (L) chains inter-connected by disulfide bonds, or an antigen binding portion thereof. Each heavy chain is comprised of a heavy chain variable region (abbreviated herein as $V_H$) and a heavy chain constant region. Each light chain is comprised of a light chain variable region (abbreviated herein as $V_L$) and a light chain constant region. The variable regions of the heavy and light chains contain a binding domain that interacts with an antigen. The $V_H$ and $V_L$ regions can be further subdivided into regions of hypervariability, termed complementarity determining regions (CDR), interspersed with regions that are more conserved, termed framework regions (FR).

The constant regions of the antibodies may mediate the binding of the immunoglobulin to host tissues or factors, including various cells of the immune system (e.g., effector cells) and the first component (Clq) of the classical complement system.

An antibody of the invention may be a monoclonal antibody or a polyclonal antibody, and will preferably be a monoclonal antibody. An antibody of the invention may be a chimeric antibody, a CDR-grafted antibody, a nanobody, a human or humanised antibody or an antigen binding portion of any thereof. For the production of both monoclonal and polyclonal antibodies, the experimental animal is typically a non-human mammal such as a goat, rabbit, rat or mouse but may also be raised in other species such as camelids.

Polyclonal antibodies may be produced by routine methods such as immunisation of a suitable animal, with the antigen of interest. Blood may be subsequently removed from the animal and the IgG fraction purified.

Monoclonal antibodies (mAbs) of the invention can be produced by a variety of techniques, including conventional monoclonal antibody methodology, e.g., the standard somatic cell hybridization technique of Kohler and Milstein. The preferred animal system for preparing hybridomas is the murine system. Hybridoma production in the mouse is a very well-established procedure and can be achieved using techniques well known in the art.

An antibody according to the invention may be produced by a method comprising: immunising a non-human mammal with an immunogen comprising full-length Lrg1, a peptide fragment of Lrg1, an epitope within the sequence of L1-24 of Appendix 2 or L94-117 of Appendix 3 (SEQ ID NO:3), L169-192 of Appendix 2 or L262-285 of Appendix 3 (SEQ ID NO:4) or L227-252 of Appendix 2 or L320-345 of Appendix 3 (SEQ ID NO:5) of Lrg1 or an epitope within other regions of Lrg1; obtaining an antibody preparation from said mammal; and deriving therefrom monoclonal antibodies that specifically recognise said epitope.

The term "antigen-binding portion" of an antibody refers to one or more fragments of an antibody that retain the ability to specifically bind to an antigen. It has been shown that the antigen-binding function of an antibody can be performed by fragments of a full-length antibody. Examples of binding fragments encompassed within the term "antigen-binding portion" of an antibody include an Fab fragment, an F(ab')$_2$ fragment, an Fab' fragment, an Fd fragment, an Fv fragment, a dAb fragment and an isolated complementarity determining region (CDR). Single chain antibodies such as scFv antibodies are also intended to be encompassed within the term "antigen-binding portion" of an antibody. These antibody fragments may be obtained using conventional techniques known to those of skill in the art, and the fragments may be screened for utility in the same manner as intact antibodies.

An antibody of the invention may be prepared, expressed, created or isolated by recombinant means, such as (a) antibodies isolated from an animal (e.g., a mouse) that is transgenic or transchromosomal for the immunoglobulin genes of interest or a hybridoma prepared therefrom, (b) antibodies isolated from a host cell transformed to express the antibody of interest, e.g., from a transfectoma, (c) antibodies isolated from a recombinant, combinatorial antibody library, and (d) antibodies prepared, expressed, created or isolated by any other means that involve splicing of immunoglobulin gene sequences to other DNA sequences.

An antibody of the invention may be a human antibody or a humanised antibody. The term "human antibody", as used herein, is intended to include antibodies having variable regions in which both the framework and CDR regions are derived from human germline immunoglobulin sequences. Furthermore, if the antibody contains a constant region, the constant region also is derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo). However, the term "human antibody", as used herein, is not intended to include antibodies in which CDR sequences derived from the germline of another mammalian species, such as a mouse, have been grafted onto human framework sequences.

Such a human antibody may be a human monoclonal antibody. Such a human monoclonal antibody may be produced by a hybridoma which includes a B cell obtained from a transgenic nonhuman animal, e.g., a transgenic mouse, having a genome comprising a human heavy chain transgene and a light chain transgene fused to an immortalized cell.

Human antibodies may be prepared by in vitro immunisation of human lymphocytes followed by transformation of the lymphocytes with Epstein-Barr virus.

The term "human antibody derivatives" refers to any modified form of the human antibody, e.g., a conjugate of the antibody and another agent or antibody.

The term "humanized antibody" is intended to refer to antibodies in which CDR sequences derived from the germline of another mammalian species, such as a mouse, have been grafted onto human framework sequences. Additional framework region modifications may be made within the human framework sequences.

Screening methods as described herein may be used to identify suitable antibodies that are capable of binding to Lrg1. Thus, the screening methods described herein may be carried out using an antibody of interest as the test compound.

Antibodies of the invention can be tested for binding to Lrg1 by, for example, standard ELISA or Western blotting. An ELISA assay can also be used to screen for hybridomas that show positive reactivity with the target protein. The binding specificity of an antibody may also be determined by monitoring binding of the antibody to cells expressing the target protein, for example by flow cytometry. Thus, a screening method of the invention may comprise the step of identifying an antibody that is capable of binding Lrg1 by carrying out an ELISA or Western blot or by flow cytometry. Antibodies having the required binding properties may then be further tested to determine their effects on the activity of Lrg1 as described further above.

Antibodies of the invention will have Lrg1 antagonist (blocking) properties as discussed above. In one embodiment, a monoclonal antibody specifically recognises an epitope within Lrg1 and blocks the activity of Lrg1. In one embodiment, the monoclonal antibody specifically recognises an epitope within Lrg1 and blocks the interaction between ALK1, TGFβRII or TGFβ and Lrg1. In one embodiment, a monoclonal antibody specifically recognises an epitope within amino acids L1-24 of Appendix 2 or L94-117 of Appendix 3 (SEQ ID NO:3), L169-192 of Appendix 2 or L262-285 of Appendix 3 (SEQ ID NO:4) or L227-252 of Appendix 2 or L320-345 of Appendix 3 (SEQ ID NO:5) and blocks the activity of Lrg1. In one embodiment, a monoclonal antibody specifically recognises an epitope within amino acids L1-24 of Appendix 2 or L94-117 of Appendix 3 (SEQ ID NO:3), L169-192 of Appendix 2 or L262-285 of Appendix 3 (SEQ ID NO:4) or L227-252 of Appendix 2 or L320-345 of Appendix 3 (SEQ ID NO:5) and blocks the interaction between ALK1, TGFβRII or TGFβ and Lrg1.

Antibodies of the invention specifically recognise Lrg1, i.e., epitopes within Lrg1. An antibody, or other compound, "specifically binds" or "specifically recognises" a protein when it binds with preferential or high affinity to the protein for which it is specific but does not substantially bind, or binds with low affinity, to other proteins. The specificity of an antibody of the invention for target protein may be further studied by determining whether or not the antibody binds to other related proteins as discussed above or whether it discriminates between them. For example, an antibody of the invention may bind to human Lrg1 but not to mouse or other mammalian Lrg1.

Antibodies of the invention will desirably bind to Lrg1 with high affinity, preferably in the picomolar range, e.g., with an affinity constant ($K_D$) of 10 nM or less, 1 nM or less, 500 pM or less or 100 pM or less, measured by surface plasmon resonance or any other suitable technique.

Once a suitable antibody has been identified and selected, the amino acid sequence of the antibody may be identified by methods known in the art. The genes encoding the antibody can be cloned using degenerate primers. The antibody may be recombinantly produced by routine methods.

Epitopes within Lrg1 can be identified by methods known in the art and discussed herein, notably by systematic screening of contiguous or overlapping peptides via a "PEP-SCAN" approach or by forming antibodies to peptide fragments (see above) shown to block Lrg1. Examples of such peptides within which epitopes can be identified for antibody production are the L1-24 of Appendix 2 or L94-117 of Appendix 3 (SEQ ID NO:3), L169-192 of Appendix 2 or L262-285 of Appendix 3 (SEQ ID NO:4) and L227-252 of Appendix 2 or L320-345 of Appendix 3 (SEQ ID NO:5) peptides discussed herein. These and other epitope-containing peptides can be used as immunogens for the generation of antibodies.

Therapeutic Indications

Any condition in which Lrg1-mediated vasculoproliferation occurs may in principle be treated, prevented or ameliorated according to the present invention. "Vasculoproliferation", "vasculoproliferative", "vasculoproliferative conditions" and similar terms as used herein encompass any and all pathologies related to the aberrant or unwanted development of blood vessels or vascular tissue or cells. For example, both pathogenic angiogenesis (the formation of new blood vessels, for example via new capillary growth from existing blood vessels) and vascular malformation (e.g., telangiectasia, the formation of dilated, tortuous and incompetent vessels, microaneurysms) can be prevented or reduced, as can neovascularisation and vascular endothelial cell proliferation. Also, as is known in the art, neoplastic growth requires the formation of new blood vessels to provide a blood supply to the growing tumour. Tumours in which Lrg1-mediated vasculoproliferation occurs are therefore also conditions which may be treated, prevented or ameliorated according to the present invention.

Preferably, there is no, or minimal effect on normal, e.g., developmental vascularisation, especially developmental vascularisation in the retina.

Treatment of ocular vasculoproliferative conditions is a preferred embodiment. Among conditions that can be treated are: diabetic retinopathy, retinal vein occlusion, retinopathy of prematurity, macular telangiectasia, age-related macular degeneration or choroidal neovascularisation.

Treatment of tumours, typically solid tumours, can also be effected, in that preventing angiogenesis in tumours derives the tumour of blood supply. Tumour treatment targets include brain, breast, kidney, colorectal, lung, prostate, head and neck, stomach, pancreatic, skin, cervical, bone, ovarian, testicular and liver tumours.

Pharmaceutical Compositions, Dosages and Dosage Regimes

Antagonists of the invention will typically be formulated into pharmaceutical compositions, together with a pharmaceutically acceptable carrier.

As used herein, "pharmaceutically acceptable carrier" includes any and all solvents, dispersion media, coatings, antibacterial and antifungal agents, isotonic and absorption delaying agents, and the like that are physiologically compatible. Preferably, the carrier is suitable for parenteral, e.g., intravenous, intramuscular, subcutaneous, intraocular or intravitreal administration (e.g., by injection or infusion). Depending on the route of administration, the modulator may be coated in a material to protect the compound from the action of acids and other natural conditions that may inactivate the compound.

The pharmaceutical compounds of the invention may include one or more pharmaceutically acceptable salts. A "pharmaceutically acceptable salt" refers to a salt that retains the desired biological activity of the parent compound and does not impart any undesired toxicological effects. Examples of such salts include acid addition salts and base addition salts.

Preferred pharmaceutically acceptable carriers comprise aqueous carriers or diluents. Examples of suitable aqueous carriers that may be employed in the pharmaceutical compositions of the invention include water, buffered water and saline. Examples of other carriers include ethanol, polyols (such as glycerol, propylene glycol, polyethylene glycol, and the like), and suitable mixtures thereof, vegetable oils, such as olive oil, and injectable organic esters, such as ethyl oleate. In many cases, it will be preferable to include isotonic agents, for example, sugars, polyalcohols such as mannitol, sorbitol, or sodium chloride in the composition.

Therapeutic compositions typically must be sterile and stable under the conditions of manufacture and storage. The composition can be formulated as a solution, microemulsion, liposome, or other ordered structure suitable to high drug concentration.

Pharmaceutical compositions of the invention may comprise additional active ingredients, notably VEGF antagonists as discussed herein.

Also within the scope of the present invention are kits comprising antagonists of the invention and instructions for use. The kit may further contain one or more additional reagents, such as an additional therapeutic or prophylactic agent as discussed above.

The antagonists and compositions of the present invention may be administered for prophylactic and/or therapeutic treatments.

In therapeutic applications, modulators or compositions are administered to a subject already suffering from a disorder or condition as described above, in an amount sufficient to cure, alleviate or partially arrest the condition or one or more of its symptoms. Such therapeutic treatment may result in a decrease in severity of disease symptoms, or an increase in frequency or duration of symptom-free periods. An amount adequate to accomplish this is defined as a "therapeutically effective amount".

In prophylactic applications, formulations are administered to a subject at risk of a disorder or condition as described above, in an amount sufficient to prevent or reduce the subsequent effects of the condition or one or more of its symptoms. An amount adequate to accomplish this is defined as a "prophylactically effective amount". Effective amounts for each purpose will depend on the severity of the disease or injury as well as the weight and general state of the subject. An example of a condition that may be treated prophylactically in the context of the invention is wet AMD (age-related macular degeneration); one eye may develop the condition before the other, with the first eye being treated once the problem is recognised and the second prophylactically.

A subject for administration of the antagonists of the invention may be a human or non-human animal. The term "non-human animal" includes all vertebrates, e.g., mammals and non-mammals, such as non-human primates, sheep, dogs, cats, horses, cows, chickens, amphibians, reptiles, etc. Administration to humans is preferred.

An antagonist of the present invention may be administered via one or more routes of administration using one or more of a variety of methods known in the art. As will be appreciated by the skilled artisan, the route and/or mode of administration will vary depending upon the desired results. Preferred routes of administration for modulators of the invention include intravenous, intramuscular, intradermal, intraocular, intraperitoneal, subcutaneous, spinal or other parenteral routes of administration, for example by injection or infusion. The phrase "parenteral administration" as used herein means modes of administration other than enteral and topical administration, usually by injection. Alternatively, an antibody of the invention can be administered via a non-parenteral route, such as a topical, epidermal or mucosal route of administration.

A suitable dosage of a modulator of the invention may be determined by a skilled medical practitioner. Actual dosage levels of the active ingredients in the pharmaceutical compositions of the present invention may be varied so as to obtain an amount of the active ingredient which is effective to achieve the desired therapeutic response for a particular patient, composition, and mode of administration, without being toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts.

A suitable dose may be, for example, in the range of from about 0.1 µg/kg to about 100 mg/kg body weight of the patient to be treated. For example, a suitable dosage may be from about 1 µg/kg to about 10 mg/kg body weight per day or from about 10 g/kg to about 5 mg/kg body weight per day. For intraocular administration, a suitable dosage may be from about 1 µg-1 mg, typically every 28 days.

Dosage regimens may be adjusted to provide the optimum desired response (e.g., a therapeutic response). For example, a single dose may be administered, several divided doses may be administered over time or the dose may be proportionally reduced or increased as indicated by the exigencies of the therapeutic situation. Dosage unit form as used herein refers to physically discrete units suited as unitary dosages for the subjects to be treated; each unit contains a predetermined quantity of active compound calculated to produce the desired therapeutic effect in association with the required pharmaceutical carrier.

Administration may be in single or multiple doses. Multiple doses may be administered via the same or different routes and to the same or different locations. Alternatively, doses can be via a sustained release formulation, in which case less frequent administration is required. Dosage and frequency may vary depending on the half-life of the antagonist in the patient and the duration of treatment desired.

As mentioned above, modulators of the invention may be co-administered with one or other more other therapeutic agents. For example, the other agent may be an analgesic, anaesthetic, immunosuppressant or anti-inflammatory agent; or a VEGF antagonist.

Combined administration of two or more agents may be achieved in a number of different ways. Both may be administered together in a single composition, or they may be administered in separate compositions as part of a combined therapy. For example, the one may be administered before, after or concurrently with the other.

Combination Therapies

As noted above, Lrg1 antagonists of the invention may be administered in combination with any other suitable active compound. In particular, because antagonism of both Lrg1 and VEGF will reduce pathogenic vascularisation, Lrg1 antagonists, notably anti-VEGF antibodies such as Avastin® and/or Lucentis® and/or receptor-based VEGF traps such as aflibercept.

The following Examples illustrate the invention.

EXAMPLES

Example 1

Gene Expression Analysis of Abnormal Retinal Vessels

Figure 1:
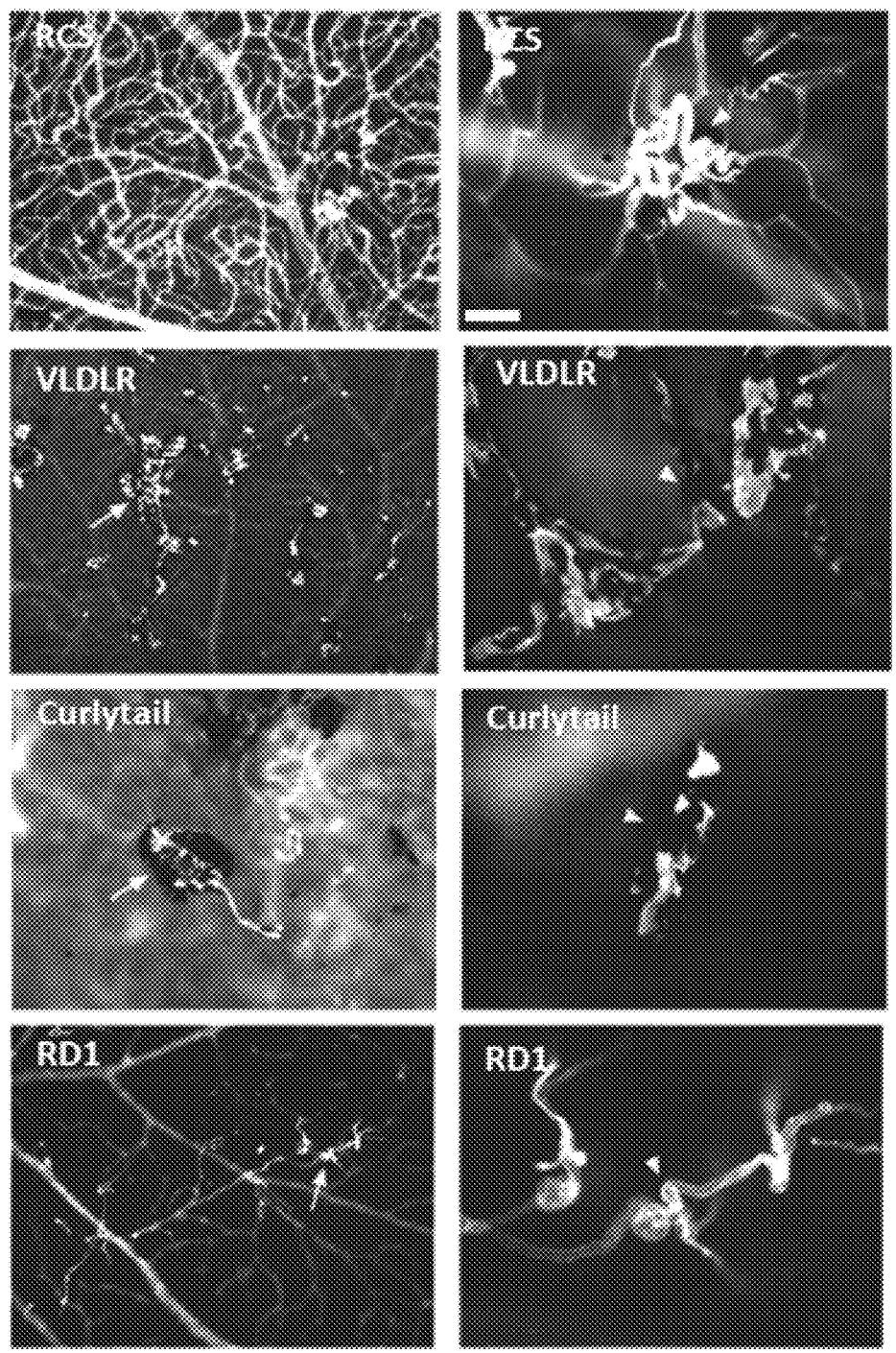
FIG. 1. Low and high power images of retinal vascular remodelling in the RCS rat (20 wks), VLDLR$^{-/-}$ mouse (16 wks), Curlytail-J mouse (13 wks) and RD1 mouse (16 wks). Vessels in retinal flat mounts were stained with anti-collagen IV and anti-claudin-5 antibodies to decorate the vascular basal lamina and endothelial cell junctions respectively.

There are various animal models of retinal disease that, despite having distinct genetic and cellular origins, exhibit an aberrant vascular response incorporating not only angiogenesis but also other vascular changes such as telangiectasia (dilated, tortuous and incompetent vessels). In order to gain new insight into the biological basis of retinal vascular remodelling we conducted a study in four of these models (FIG. 1) whereby we investigated the differential expression of genes in pathogenic retinal microvessels compared to microvessels from normal controls. Isolated and purified microvessel fragments from the retinae of wild type (WT) mice, retina dystrophy (RD) 1 mice, curlytail (CT) mice and very-low density lipoprotein receptor (VLDLR) knock-out mice at time points corresponding to stages when vascular anomalies were present were investigated. Microarray gene expression analysis (Affymetrix®) on isolated RNA from the three mouse models revealed 63 genes common to all that were either up- or down-regulated in the microvessels from diseased retina (FIG. 10). Of the 63 genes differentially expressed in the retinal vasculature of the three mouse models of vascular remodelling, leucine-rich alpha-2-glycoprotein-1 (Lrg1) was ranked the most significant (following FDR analysis). Lrg1 is a secreted glycoprotein (FIG. 2) of the leucine-rich repeat family of proteins which are involved in protein-protein interactions, signalling and cell adhesion and development.

Example 2

Validation of Lrg1 Overexpression Observed in Microarray Data

The increased expression of Lrg1 in the retina of the mouse models was validated first by quantitative PCR. mRNA from whole retina of WT, RD1, CT and VLDLR−/− mice was extracted and subjected to quantitative real time PCR (qRTPCR). As indicated by microarray analysis the qRTPCR demonstrated that there was a significant (p<0.05) increase in transcript expression of Lrg1 in the three models of retinal vascular pathology when compared to control mice (FIG. 3A). To establish that the increase in mRNA translated into increased protein expression we next isolated retinas at identical time-points to the gene expression studies and prepared the tissue for protein analysis by western blot (FIG. 3B). Semi-quantification of the western blot data (n>3) by densitometric analysis compared to a housekeeping protein (GAPDH) revealed significant increases in Lrg1 protein expression (p<0.05). To determine the distribution of Lrg1 in the retinal vasculature and to establish whether other cells of the retina express Lrg1 we carried out in situ hybridisation and immunohistochemistry to detect Lrg1 mRNA and protein respectively. In normal mice Lrg1 mRNA (FIG. 3C) and protein (FIG. 3D) were expressed predominantly by the vasculature.

Example 3

Lrg1 Associates with the TGFβ Receptors TGFβRII and ALK1

Virtually nothing is known regarding the biology of Lrg1. Several reports have described concomitant increases in the level of expression of TGFβ1, TIβR-II and Lrg1 in a number of diseases (Sun et al., 1995; Li et al., 2007). This is particularly germane as dysfunction of TGFβ signalling in endothelial cells leads to the disease Hemorrhagic Hereditary Telangiectasia (HHT). In this group of diseases, which are characterised by vascular abnormalities including telangiectasis, mutations in the TGFβ endothelial accessory receptor endoglin and the TGFβ type I receptor ALK1 lead to HHT1 (McAllister et al. 1994) and HHT2 (Johnson et al. 1995) respectively. Moreover, we have pilot data in VLDLR-/- mice to the effect that TGFβ mRNA increases significantly in retinal tissue, but not RPE or microvessels. Of further relevance, TGFβ has been found to be increased in the retinas of patients with diabetic retinopathy (Spirin et al., 1999) where vascular remodelling is prevalent.

In endothelial cells TGFβ signaling can occur through TGFβ receptor II associating either with the ubiquitous TGFβ type I receptor activin receptor-like kinase 5 (ALK5) or ALK1, which is expressed primarily in endothelial cells, with the cellular response depending on which pathway predominates. In the case of ALK5 there is increased ECM deposition and cell quiescence whilst with ALK1 there is endothelial cell activation manifest as increased migration and proliferation. This differential signalling is partly controlled by the concentration/bioavailability of TGFβ and by members of a family of downstream effector proteins called Smads, whereby Smads 2 and 3 associate with ALK5, and Smads 1, 5 and 8 with ALK1. We have explored the connection between Lrg1 and the TGF signalling pathway. We first established that a rat brain endothelial cell line (GPNT) expressed both Lrg1, TGFβRII as well as other components of TGFβ signalling (see appendix 1). We demonstrated that immunoprecipitation of Lrg1 from GPNT cell lysates resulted in co-precipitation of the receptors TGFβRII and ALK1 (FIG. 4A). Similarly, immunoprecipitation of either TGFβRII or ALK1 resulted in co-precipitation of Lrg1 indicating that Lrg1 associates with both receptors (FIG. 4A). We have also shown that HA-tagged recombinant Lrg1 protein from bacteria associates with TGFβRII and TGFβ (FIG. 4B). In addition, immunocytochemical visualisation of Lrg1 and TGFβRII expression on GPNT cells demonstrates co-localisation (FIG. 4C). We hypothesise, therefore, that Lrg1 acts as a modulator of TGFβ signalling causing fine-tuning between TGFβRII and the ALK1 and ALK5 activated signalling cascades. We also have shown that TGFβ induces Lrg1 gene expression in GPNT cells suggesting a possible feedback mechanism (FIG. 16).

Example 4

Lrg1 Modifies TGFβ Signalling Through Differential Smad Phosphorylation

To establish whether Lrg1 affects TGFβ-mediated vascular endothelial cell responses we next knocked down Lrg1 in GPNT cells with siRNA and determined its effects on TGFβ-mediated cell proliferation. In control cells TGFβ induces a significant increase (p<0.05) in endothelial cell proliferation (70% confluent cells) over a 2 hour period. Lrg1 knockdown in GPNT endothelial cells with siRNA blocks this TGFβ-mediated increase in cell proliferation (FIGS. 6A and B). This correlated with a reduction in Smad5 phosphorylation (FIG. 4D). Conversely, in GPNT cells transfected with the Lrg1 gene we show that Lrg1 overexpression leads to enhanced endothelial cell proliferation in response to TGFβ (FIGS. 6A and B). This enhanced response correlates with a down-regulation in Smad2 expression and increased Smad5 phosphorylation (FIG. 4E). These data are consistent with decreased signalling via the TGFβRII/ALK5 receptor complex pathway and hence a shift towards activation of the vasculopathogenic TGFβRII/ALK1 signalling pathway.

Example 5

Lrg1 Conditioned Medium Enhances Angiogenesis in Vitro

Having established that Lrg1 modifies TGFβ signalling in endothelial cells and affects TGFβ-mediated cell proliferation we next determined whether Lrg1 impacts on angiogenesis using a standard in vitro angiogenesis assay. Human umbilical vein endothelial cells (HUVEC) were grown in Matrigel™ and subjected to unconditioned growth media, media conditioned by GPNT cells (which constitutively secrete Lrg1) and media conditioned by GPNT cells overexpressing Lrg1. Control media contained no Lrg1 whilst GPNT and Lrg1 over-expressing GPNT media contained moderate and high levels of Lrg1 respectively (FIG. 7B). The degree of vascular formation was greatest when conditioned medium from Lrg1 over-expressing cells was added (FIGS. 7A and C). The increased vascularisation correlated with Lrg1 protein expression in the medium.

Example 6

Peptide Sequence L227-252 of Appendix 2 (SEQ ID NO:5) or L320-345 of Appendix 3 (SEQ ID NO:5) Derived from Lrg1 Modifies TGFβ Signalling in GPNT Cells We next established whether we could block endothelial Smad5 phosphorylation induced by TGFβ with either an anti-Lrg1 antibody or by peptide sequences derived from Lrg1. Peptides derived from the leucine-rich repeat regions of the Lrg1 sequence (L1-24 and L169-192 of Appendix 2 (SEQ ID NOS:3-4) or L94-117 and L262-285 of Appendix 3 (SEQ ID NOS:3-4)), which are believed to be involved in protein-protein interactions, and from the highly conserved leucine-rich C-terminal domain (L227-252 of Appendix 2 (SEQ ID NO:5) or L320-345 of Appendix 3 (SEQ ID NO:5)) were generated (Appendix 2). Lrg1 over-expression in GPNT cells did not result in Smad5 phosphorylation. Treatment of control cells with 5 ng/ml TGFβ results in a significant increase in Smad5 phosphorylation. In the Lrg1 over-expressing cells the effect of TGFβ on Smad5 phosphorylation is significantly enhanced. When the Lrg-1 over-expressing endothelial cells were co-treated with the anti-Lrg1 polyclonal antibody there was a decrease in the level of Smad5 phosphorylation suggesting that the antibody is capable of interfering with Lrg1 interactions. Co-treatment with the peptides had variable effects with peptide L1-24 of Appendix 2 (L94-117 of Appendix 3) (SEQ ID NO:3) having no effect on Smad5 phosphorylation, peptide L169-192 of Appendix 2 (L262-285 of Appendix 3) (SEQ ID NO:4) had a partial effect whilst peptide L227-252 of Appendix 2 (L320-345 of Appendix 3) (FIG. 5) (SEQ ID NO:5) had a dramatic inhibitory effect. Combination of all three peptides almost completely abolished TGFβ mediated Smad5 phosphorylation. These data support the hypothesis that Lrg1 modifies TGFβ mediated signalling and that Lrg1 antagonists can be used as therapeutic agents.

Example 7

Aortic Rings from Lrg1 Knockout Mice Display Reduced Angiogenic Vessel Sprouting The role of Lrg1 in angiogenesis in vivo was then examined. Thoracic aortas were removed from P14 Lrg1 knock-out mice or wild type littermate controls sacrificed by cervical dislocation and immediately transferred to a culture dish containing ice-cold serum-free OPTI-MEM® (Invitrogen). The peri-aortic fibroadipose tissue was carefully removed with fine microdissecting forceps. One millimeter long aortic rings were sectioned and embedded in a rat tail collagen I gel (1.5 mg/ml) prepared in DMEM at pH 7.4. The collagen gels containing the aortic rings were kept at 37° C. in 96 well plates for 7 days. Each well contained endothelial cell basal medium supplemented with 2.5% FCS, 100 U/ml penicillin and 100 μg/ml streptomycin. Images were taken with an Olympus microscope.

The number of angiogenic vessels sprouting from each aortic ring was quantified. Aortic rings isolated from both mice heterozygous and homozygous for the Lrg1 gene knockout exhibited significantly reduced angiogenic vessel sprouting compared to aortic rings from wild type mice (p<0.01) (FIG. 9).

Example 8

Choroidal Neovascularisation (CNV) After Retinal Injury is Reduced in Lrg1 Knockout Mice Bruch's membrane was ruptured by laser at three locations surrounding the optic nerve in each eye of Lrg1 knock-out mice or wild-type littermate controls. The CNV lesions at Bruch's membrane rupture sites were measured 1 week after laser treatment by in vivo fundus fluorescein angiography (FA). Fluorescein was delivered through intraperitoneal injection. Early and late-phase fundus angiograms were obtained at an interval of 7 minutes. The early phase angiogram was obtained 90 seconds after injection indicating the size of choroidal neovascularisation. The late phase angiogram demonstrates leakage from choroidal neovascular membrane.

The FA clearly showed that choroidal neovascularisation was reduced in the Lrg1 knockout mice (FIG. 11A). Quantification of the choroidal neovasculature revealed that the size of the area of angiogenic growth and leakage was significantly reduced in the Lrg1 knockout as compared to the wild type mice (FIGS. 11B and C) (**p<0.01).

Example 9

Retinal Neovascularisation Following Oxygen-Induced Retinopathy (OIR) is Reduced in Lrg1 Knockout Mice P7 Lrg1 knock-out mice and wild-type littermate controls with nursing mothers were subjected to hyperoxia (75% oxygen) for 5 days, which leads in the neonates to significant inhibition of retinal vessel development. On P12, mice were returned to normoxia whereupon the hypoxic avascular retina triggers both normal vessel regrowth and pathological neovascularisation, which reaches a peak at P17. Retinas were isolated, fixed and subjected to whole mount immunostaining using isolectin-B4 (FIG. 13A). Vascular regrowth was quantified by comparing the avascular area to total retinal area. Neovascularisation was quantified by manually measuring the area of neovascular tufts.

The size of the avascular region was found to be significantly increased in the retinas of Lrg1 knockout mice (*p<0.05) (FIG. 13B). Also, the number of neovascular tufts was significantly reduced in the Lrg1 knockout mice as compared to the wild type mice (**p<0.002) (FIG. 13C).

Example 10

Tube, Cord and Vessel Formation of Human Umbilical Vein Endothelial Cells (HUVEC) in Matrigel™ in vitro is Reduced by the Addition of a Polyclonal Anti-Lrg1 Antibody In vitro tube formation assays were carried out in Matrigel™ using Human Umbilical Vein Endothelial Cells (HUVEC). 96-well plates were coated with 60 μl of Matrigel™ per well. Each well was treated with 100 μl of EGM2 medium containing 15,000 HUVEC in the presence of 100 nM of anti-human polyclonal Lrg1 antibody (raised against the whole Lrg1 glycoprotein), 100 nM isotype IgG or equivalent volume of antibody elution buffer for 16 hours at 37° C., 5% $CO_2$. Cells were washed and fixed. Tube formation was significantly reduced by the addition of a neutralizing anti-human Lrg1 polyclonal antibody, compared with the addition of antibody elution buffer (p<0.01) or compared with the addition of an irrelevant IgG antibody (p<0.05). Tube formation was measured by the number of branch points (FIG. 14A) tube number (FIG. 14A) and total tube length (FIG. 14B).

Example 11

Lrg1 and TGFβ Expression in the Vitreous Humour is Increased in Human Patients Suffering from Proliferative Diabetic Retinopathy (PDR)

Immunohistochemical analysis of a human retina was conducted, with staining for Lrg1 detected in the retinal vasculature (FIG. 15A). Samples of vitreous humour were obtained from non-diabetic patients and patients suffering from PDR. The presence of Lrg1 in the vitreous samples was determined using western blotting and quantified by densitometric analysis (FIG. 15B). Lrg1 was significantly increased in the vitreous of patients suffering from PDR compared to non-diabetic patients ($p<0.01$). The presence of TGFβ in the vitreous samples was also determined by western blotting and quantified as for Lrg1 (FIG. 15C). TGFβ was also significantly increased in patients suffering from PDR ($p<0.01$).

The present inventors have therefore demonstrated that reduced Lrg1 expression is associated with a reduced angiogenic response to retinal trauma. Lrg1 and TGFβ have also been shown to be up-regulated in patients suffering from PDR, a condition characterised by an increase in retinal neovascularisation. This supports the hypothesis that Lrg1 is involved in stimulating vasculoproliferation via TGFβ-mediated signalling, and that Lrg1 antagonists, especially antibodies, can be used as therapeutic agents to combat undesired vascular proliferation.

APPENDIX 1

| Probe | Symbol | Description | $Log_2$ Fold Change_CT | $Log_2$ Fold Change_RD1 | $Log_2$ Fold Change_VLDLR |
|---|---|---|---|---|---|
| 1417290_at | Lrg1 | leucine-rich alpha-2-glycoprotein 1 | 6.519850734 | 3.816848952 | 5.777919149 |
| 1418090_at | Plvap | plasmalemma vesicle associated protein | 4.737700645 | 2.015383555 | 4.015170052 |
| 1444552_at | BC032203 | cDNA sequence BC032203 | −3.416739788 | −4.125380964 | −2.568344913 |
| 1428909_at | A130040M12Rik | RIKEN cDNA A130040M12 gene | 3.311352995 | 2.649653567 | 2.11155484 |
| 1438651_a_at | Agtrl1 | angiotensin receptor-like 1 | 3.055248193 | 3.156981806 | 3.430316425 |
| 1448550_at | Lbp | lipopolysaccharide binding protein | 3.054367211 | 3.692692577 | 3.827068592 |
| 1441789_at | Rsbn1 | rosbin, round spermatid basic protein 1 | −3.030865082 | −3.9006414 | −2.474550588 |
| 1421813_a_at | Psap | prosaposin | 2.665924081 | 1.259509319 | 1.277641505 |
| 1417314_at | Cfb | complement factor B | 2.647126931 | 1.89078393 | 2.247410862 |
| 1441593_at | Pten | phosphatase and tensin homolog | −2.536206087 | −4.361535072 | −3.214444147 |
| 1440068_at | Rfxdc2 | regulatory factor X domain containing 2 homolog (human) | −2.384035095 | −1.179261665 | −3.066735413 |
| 1455396_at | Atp8b1 | ATPase, class I, type 8B, member 1 | 2.023505786 | 2.272847784 | 2.266282648 |
| 1445746_at | Rad52 | RAD52 homolog (S. cerevisiae) | −1.954283912 | −2.172837472 | −2.156662562 |
| 1447024_at | | | −1.818125782 | −2.036684918 | −1.892365323 |
| 1441671_at | Glcci1 | glucocorticoid induced transcript 1 | −1.775990978 | −2.213802579 | −2.277307668 |
| 1458068_at | 4932417H02Rik | RIKEN cDNA 4932417H02 gene | −1.774932834 | −2.309095175 | −1.631838059 |
| 1446516_at | Gltscr1 | glioma tumor suppressor candidate region gene 1 | −1.72511362 | −2.804674797 | −1.936973954 |
| 1429113_at | 1500031I19Rik | RIKEN cDNA 1500031I19 gene | −1.723237635 | −1.667727966 | −1.844864996 |
| 1444599_at | | | −1.705821329 | −1.091181534 | −1.206897797 |
| 1442411_at | Glcci1 | glucocorticoid induced transcript 1 | −1.672238827 | −1.699029862 | −1.347063782 |
| 1442548_at | Crim1 | cysteine rich transmembrane BMP regulator 1 (chordin like) | −1.653036647 | −1.940264082 | −1.740841839 |
| 1442278_at | Jarid1b | jumonji, AT rich interactive domain 1B (Rbp2 like) | −1.593241687 | −2.054920044 | −1.592312043 |
| 1436892_at | Spred2 | sprouty-related, EVH1 domain containing 2 | −1.560872761 | −2.239579229 | −1.384970196 |
| 1424374_at | Gimap4 | GTPase, IMAP family member 4 | 1.514592532 | 1.668786796 | 1.643819758 |
| 1458798_at | BC032203 | cDNA sequence BC032203 | −1.50571231 | −1.466939411 | −1.184280404 |
| 1460567_at | Rfxdc2 | regulatory factor X domain containing 2 homolog (human) | −1.494802256 | −1.825546132 | −1.956274263 |
| 1437937_at | Ccbp2 | chemokine binding protein 2 | 1.471971509 | 0.99575522 | 1.086669094 |
| 1442735_at | Oaz2 | ornithine decarboxylase antizyme 2 | −1.449026953 | −1.633794668 | −1.456998627 |
| 1418133_at | Bcl3 | B-cell leukemia/lymphoma 3 | 1.433022778 | 0.726805713 | 1.171794534 |
| 1423082_at | Derl1 | Der1-like domain family, member 1 | 1.399246787 | 0.852655229 | 0.835345089 |
| 1459687_x_at | Cpsf6 | cleavage and polyadenylation specific factor 6 | −1.392466072 | −2.325957358 | −1.608667724 |
| 1457477_at | Mbnl2 | muscleblind-like 2 | −1.296353942 | −2.573702542 | −1.546880217 |
| 1440755_at | Nbr1 | neighbor of Brca1 gene 1 | −1.12906095 | −1.532910502 | −1.10552062 |
| 1446954_at | Pdha1 | pyruvate dehydrogenase E1 alpha 1 | −1.123702369 | −1.370689608 | −1.284670518 |

APPENDIX 1-continued

| Probe | Symbol | Description | Log₂ Fold Change_CT | Log₂ Fold Change_RD1 | Log₂ Fold Change_VLDLR |
|---|---|---|---|---|---|
| 1429117_at | Tradd | TNFRSF1A-associated via death domain | 1.111236473 | 1.435822999 | 1.068334016 |
| 1437965_at | Heatr1 | HEAT repeat containing 1 | −1.09095976 | −1.939819175 | −1.349663136 |
| 1432978_at | 9030607L02Rik | RIKEN cDNA 9030607L02 gene | −1.068488611 | −0.886239428 | −0.866281171 |
| 1451486_at | 1200006F02Rik | RIKEN cDNA 1200006F02 gene | 1.065952649 | 0.786730964 | 0.940147563 |
| 1420886_a_at | Xbp1 | X-box binding protein 1 | 1.023069178 | 1.011010936 | 0.941050305 |
| 1445436_at | | | −1.014077281 | −0.934117344 | −0.705298896 |
| 1435984_at | 1110033F14Rik | RIKEN cDNA 1110033F14 gene | −1.008999711 | −0.76932415 | −1.615279068 |
| 1455611_at | Pias1 | protein inhibitor of activated STAT 1 | −0.908527509 | −0.538998769 | −0.692698458 |
| 1426287_at | Atxn7 | ataxin 7 | −0.879594769 | −1.096312483 | −0.961142854 |
| 1428996_at | 4833426J09Rik | RIKEN cDNA 4833426J09 gene | −0.866335737 | −0.683423202 | −1.239422567 |
| 1445438_at | Ddhd1 | DDHD domain containing 1 | −0.846768882 | −1.091162548 | −0.76202582 |
| 1420011_s_at | Xbp1 | X-box binding protein 1 | 0.839346345 | 0.751048508 | 0.589687416 |
| 1431146_a_at | Cpne8 | copine VIII | 0.777306593 | 0.820922725 | 1.084920536 |
| 1442071_at | Abce1 | ATP-binding cassette, sub-family E (OABP), member 1 | −0.774526167 | −1.223847712 | −0.713864956 |
| 1433954_at | 4632419I22Rik | RIKEN cDNA 4632419I22 gene | 0.731805211 | 0.848318756 | 0.778790464 |
| 1451160_s_at | Pvr | poliovirus receptor | 0.713272364 | 0.861839016 | 1.056537225 |
| 1420475_at | Mtpn | myotrophin | 0.711778746 | 0.709146206 | 0.708281895 |
| 1440331_at | 9430079B08Rik | RIKEN cDNA 9430079B08 gene | −0.711608755 | −0.533392331 | −0.57158557 |
| 1419236_at | Helb | helicase (DNA) B | −0.70643309 | −1.279893048 | −0.820431257 |
| 1422470_at | Bnip3 | BCL2/adenovirus E1B interacting protein 1, NIP3 | 0.69318397 | 1.136323881 | 0.979461584 |
| 1419104_at | Abhd6 | abhydrolase domain containing 6 | 0.621125798 | 0.440366945 | 0.495717954 |
| 1418621_at | Rab2 | RAB2, member RAS oncogene family | 0.616966306 | 0.874125971 | 0.705527995 |
| 1428090_at | Ptcd3 | Pentatricapeptide repeat domain 3 | 0.536426675 | 0.621367847 | 0.509893114 |
| 1437919_at | Bdp1 | B double prime 1, subunit of RNA polymerase III transcription initiation factor IIIB | −0.531772283 | −0.580166221 | −0.46515885 |
| 1442443_at | Sync | syncoilin | −0.530476172 | −0.605230238 | −0.624932339 |
| 1460585_x_at | Pisd | phosphatidylserine decarboxylase | 0.474374089 | 0.433538341 | 0.538623288 |
| 1432271_a_at | Dcun1d5 | DCN1, defective in cullin neddylation 1, domain containing 5 (*S. cerevisiae*) | 0.467526394 | 0.760717934 | 0.615251382 |
| 1418437_a_at | Mlx | MAX-like protein X | 0.396356101 | 0.75831887 | 0.46866585 |

APPENDIX 2

```
M1rg1    1      LRELHLSSNRLQALSPELLAPVPR              24
                L+ELHLSSN L++LSPE L PVP+
HLrg1    1      LQELHLSSNGLESLSPEFLRPVPQ              24

M1rg1    25     LRALDLTRNALRSLPPGLFSTSAN              48
                LR LDLTRNAL  LPPGLF  SA
HLrg1    25     LRVLDLTRNALTGLPPGLFQASAT              48

M1rg1    49     LSTLVLRENQLREVSAQWLQGLDA              72
                L TLVL+ENQL   +  WL GL A
HLrg1    49     LDTLVLKENQLEVLEVSWLHGLKA              72

M1rg1    73     LGHLDLAENQLSSLPSGLLASLGA              96
                LGHLDL+ N+L  LP GLLA+
HLrg1    73     LGHLDLSGNRLRKLPPGLLANFTL              96

M1rg1    97     LHTLDLGYNLLESLPEGLLRGPRR             120
                L TLDLG N LE+LP  LLRGP+
HLrg1    97     LRTLDLGENQLETLPPDLLRGPLQ             120

M1rg1    121    LQRLHLEGNRLQRLEDSLLAPQPF             144
                L+RLHLEGN+LQ  L  LL PQP
HLrg1    121    LERLHLEGNKLQVLGKDLLLPQPD             144
```

APPENDIX 2-continued

```
M1rg1    145    LRVLFLNDNQLVGVATGSFQGLQH                   168
                LR LFLN N+L  VA G+FQGL+
HLrg1    145    LRYLFLNGNKLARVAAGAFQGLRQ                   168

M1rg1    169    LDMLDLSNNSLSSTPPGLWAFLGR                   192
                LDMLDLSNNSL+S P GLWA LG+
HLrg1    169    LDMLDLSNNSLASVPEGLWASLGQ                   192

M1rg1    193    PTRDMQDGFDISHNPWICDKNLADLCRWLVANRN          226
                P DM + DGFDIS NPWICD +NL +DL RWL A++
HLrg1    193    PNWDMRDGFDISGNPWICDQNLSDLYRWLQAQKD          226

M1rg1    227    KMFSQNDTRCAGPEAMKGQRLLDVAE  (SEQ ID NO: 9) 252
                KMFSQNDTRCAGPEA +KGQ LL VA+
HLrg1    227    KMFSQNDTRCAGPEAVKGQILLAVAK  (SEQ ID NO: 8) 252

L1-24:      LQELHLSSNGLESLSPEFLRPVPQ  (SEQ ID NO: 3)

L169-192:   LDMLDLSNNSLASVPEGLWASLGQ  (SEQ ID NO: 4)

L227-252:   KMFSQNDTRCAGPEAVKGQTLLAVAK  (SEQ ID NO: 5)
```

Partial sequence alignment of mouse (SEQ ID NO:9) and human Lrg1 (SEQ ID NO:8), arranged to illustrate the leucine-rich repeats in bold, and the highly conserved C-terminal domains as double underlined text.

Leucine-rich α-2-glycoprotein 1 (Lrg1) exhibited the greatest fold change in the remodelled retinal vessels. Aligned amino acid sequence of human and mouse Lrg1. In bold are the leucine rich repeat regions and double under

APPENDIX 3

```
Human    1      MSSWSRQRPK   SPGGIQPHVS   RTLFLLLLLA   ASAWGVTLSP
                M  SW Q                   L  LL            G    S
Mouse    1      MVSWQHQGSL   QDLKTCLART   LFLLALL---   ----GRVSSL Human    41     KDCQVFRSDH   GSSISCQPPA   EIPGYLPADT   VHLAVEFFNL
                K+C + +S     GS++SC  P    E P  LPADT    VHL+VEF NL
Mouse    34     KECLILQSAE   GSTVSCHGPT   EFPSSLPADT   VHLSVEFSNL Human    81     THLPANLLQG   ASKLQELHLS   SNGLESLSPE   FLRPVPQLRV
                T LPA  LQG     L+ELHLS    SN L++LSPE    L PVP+LR
Mouse    74     TQLPAAALQG   CPGLRELHLS   SNRLQALSPE   LLAPVPRLRA Human    121    LDLTRNALTG   LPPGLFQASA   TLDTLVLKEN   QLEVLEVSWL
                LDLTRNAL     LPPGLF  SA   L TLVL+EN    QL  +  WL
Mouse    114    LDLTRNALRS   LPPGLFSTSA   NLSTLVLREN   QLREVSAQWL Human    161    HGLKALGHLD   LSGNRLRKLP   PGLLANFTLL   RTLDLGENQL
                 GL ALCHLD   L+ N+L  LP   GLLA+   L    TLDLG N L
Mouse    154    QGLDALGHLD   LAENQLSSLP   SGLLASLGAL   HTLDLGYNLL Human    201    ETLPPDLLRG   PLQLERLHLE   GNKLQVLGKD   LLLPQPDLRY
                E+LP  LLRGP   +L+RLHLE   GN+LQ L     LL PQP  LR
Mouse    194    ESLPEGLLRG   PRRLQRLHLE   GNRLQRLEDS   LLAPQPFLRV Human    241    LFLNGNKLAR   VAAGAFQGLR   QLDMLDLSNN   SLASVPEGLW
                LFLN N+L     VA G+FQGL+      LDMLDLSNN   SL+S P GLW
Mouse    234    LFLNDNQLVG   VATGSFQGLQ   HLDMLDLSNN   SLSSTPPGLW Human    281    ASLGQPNWDM   RDGFDISGNP   WICDQNLSDL   YRWLQAQKDK
                A LG+P  DM   +DGFDIS NP   WICD NL+DL    RWL A ++K
Mouse    274    AFLGRPTRDM   QDGFDISHNP   WICDKNLADL   CRWLVANRNK Human    321    MFSQNDTRCA   GPEAVKGQTL   LAVAKSQ       (SEQ ID NO: 2)
                MFSQNDTRCA   GPEA+KGQ L   L VA+
Mouse    314    MFSQNDTRCA   GPEAMKGQRL   LDVAELGSL     (SEQ ID NO: 6)
``` lined is the human C-terminal domain region used as a blocking peptide.

REFERENCES

Isolation and characterization of an unknown, leucine-rich 3.1-S-alpha2-glycoprotein from human serum: Haupt H, Baudner S; Hoppe Seylers Z Physiol Chem. 1977 June; 358(6): 639-46. (Title translated from original German).

Periodicity of leucine and tandem repetition of a 24-amino acid segment in the primary structure of leucine-rich alpha 2-glycoprotein of human serum: Takahashi N, Takahashi Y, Putnam F W; Proc Natl Acad Sci USA. 1985 April; 82(7):1906-10.

Differentially expressed genes in TGF-beta 1 sensitive and resistant human hepatoma cells: Sun D, Kar S, Can B I; Cancer Lett. 1995 Feb. 10; 89(1):73-9.

Expression of TGF-betas and TGF-beta type II receptor in cerebrospinal fluid of patients with idiopathic normal pressure hydrocephalus: Li X, Miyajima M, Jiang C, Arai H; Neurosci Lett. 2007 Feb. 14; 413(2):141-4. Epub 2006 Dec. 27.

Identification of putative serum glycoprotein biomarkers for human lung adenocarcinoma by multilectin affinity chromatography and LC-MS/MS: Heo S H, Lee S J, Ryoo H M, Park J Y, Cho J Y.; Proteomics. 2007 December; 7(23):4292-302.

Increased expression of one isoform of leucine-rich alpha-2-glycoprotein in peritoneal fluid of women with uterine leiomyomas: Ferrero S, Gillott D J, Remorgida V, Anserini P, Ragni N, Grudzinskas J G; Arch Gynecol Obstet. 2009 March; 279(3):365-71. Epub 2008 Jul. 30.

Potential diagnostic biomarkers in serum of idiopathic pulmonary arterial hypertension: Zhang J, Zhang Y, Li N, Liu Z, Xiong C, Ni X, Pu Y, Hui R, He J, Pu J.; Respir Med. 2009 Aug. 22. [Epub ahead of print]

Endoglin, a TGF-beta binding protein of endothelial cells, is the gene for hereditary haemorrhagic telangiectasia type 1. McAllister K A, Grogg K M, Johnson D W, Gallione C J, Baldwin M A, Jackson C E, Helmbold E A, Markel D S, McKinnon W C, Murrell J, et al. Nat Genet. 1994 December; 8(4):345-51.

A second locus for hereditary hemorrhagic telangiectasia maps to chromosome 12. Johnson D W, Berg J N, Gallione C J, McAllister K A, Warner J P, Helmbold E A, Markel D S, Jackson C E, Porteous M E, Marchuk D A. Genome Res. 1995 August; 5(1):21-8.

Basement membrane and growth factor gene expression in normal and diabetic human retinas. Spirin K S, Saghizadeh M, Lewin S L, Zardi L, Kenney M C, Ljubimov A V. Curr Eye Res. 1999 June; 18(6):490-9.

Plasma proteomics of pancreatic cancer patients by multi-dimensional liquid chromatography and two-dimensional difference gel electrophoresis (2D-DIGE): up-regulation of leucine-rich alpha-2-glycoprotein in pancreatic cancer. Kakisaka T, Kondo T, Okano T, Fujii K, Honda K, Endo M, Tsuchida A, Aoki T, Itoi T, Moriyasu F, Yamada T, Kato H, Nishimura T, Todo S, Hirohashi S. J Chromatogr B Analyt Technol Biomed Life Sci. 2007 Jun. 1; 852(1-2):257-67. Epub 2007 Feb. 1.

US 2005/0064516
WO 2008/092214
US 2007/0184503
Sequence Information
Sequences of Human Lrg1
SEQ ID NO:1—DNA Sequence of Human Lrg1

[Sequence encoding protein of SEQ ID NO:2 is bold and underlined within SEQ ID NO:1 below]

GCAGAGCTACCATGTCCTCTTGGAGCAGACAGCGACCAAAAAGCCC
AGGGGGCATTCAACCCCATGTTTCTAGAACTCTGTTCCTGCTGCTG
CTGTTGGCAGCCTCAGCCTGGGGGGTCACCCTGAGCCCCAAAGACT
GCCAGGTGTTCCGCTCAGACCATGGCAGCTCCATCTCCTGTCAACC
ACCTGCCGAAATCCCCGGCTACCTGCCAGCCGACACCGTGCACCTG
GCCGTGGAATTCTTCAACCTGACCCACCTGCCAGCCAACCTCCTCC
AGGGCGCCTCTAAGCTCCAAGAATTGCACCTCTCCAGCAATGGGCT
GGAAAGCCTCTCGCCCGAATTCCTGCGGCCAGTGCCGCAGCTGAGG
GTGCTGGATCTAACCCGAAACGCCCTGACCGGGCTGCCCCCGGGCC
TCTTCCAGGCCTCAGCCACCCTGGACACCCTGGTATTGAAAGAAAA
CCAGCTGGAGGTCCTGGAGGTCTCGTGGCTACACGGCCTGAAAGCT
CTGGGGCATCTGGACCTGTCTGGGAACCGCCTCCGGAAACTGCCCC
CCGGGCTGCTGGCCAACTTCACCCTCCTGCGCACCCTTGACCTTGG
GGAGAACCAGTTGGAGACCTTGCCACCTGACCTCCTGAGGGGTCCG
CTGCAATTAGAACGGCTACATCTAGAAGGCAACAAATTGCAAGTAC
GTGGGAAAAGATCTCCTCTTGCCGCAGCCGGACCTGCGCTACCTCT
TCCTGAACGCAACAAGCTGGCCAGGGTGGCAGCCGGTGCCTTCCAG
GGCCTGCGGCAGCTGGACATGCTGGACCTCTCCAATAACTCACTGG
CCAGCGTGCCCGAGGGGCTCTGGGCATCCCTAGGGCAGCCAAACTG
GGACATGCGGGATGGCTTCGACATCTCCGGCAACCCCTGGATCTGT
GACCAGAACCTGAGCGACCTCTATCGTTGGCTTCAGGCCCAAAAAG
ACAAGATGTTTCCCAGAATGACACGCGCTGTGCTGGGCCTGAAGC
CGTGAAGGGCCAGACGCTCCTGGCAGTGGCCAAGTCCCAGTGAGAC
CAGGGGCTTGGGTTGAGGGTGGGGGGTCTGGTAGAACACTGCAACC
CGCTTAACAAATAATCCTGCCTTTGGCCGGGTGCGGGGCTCACGC
CTGTAATCCCAGCACTTTGGGAGGCCCAGGTGGGCGGATCACGAGG
GTCAGGAGATCGAGACCATCTTGGCTAACATGGTAAACCCTGTCTC
TACTAAAAATATAAAAAATTAGCCAGGCGTGGTGGTGGGCACCTGT
AGTCCCAGCAACTCGGGAGGCTGAGGCAGGAGAATGGCGTGAACTT
GGGAGGCGGAGCTTGCGGTGAGCCAAGATCGTGCCACTGCACTCTA
GCCTGGGCGACAGAGCAAGACTGTCTCAAAAAAATTAAAATTAAAA
TTAAAAACAAATAATCCTGCCTTTTACAGGTGAAACTCGGGGCTGT
CCATAGCGGCTGGGACCCCGTTTCATCCATCCATGCTTCCTAGAAC
ACACGATGGCTTTCCTTACCCATGCCCAAGGTGTGCCCTCCGTCT
GGAATGCCGTTCCCTGTTTCCCAGATCTCTTGAACTCTGGGTTCTC
CCAGCCCCTTGTCCTTCCTTCCAGCTGAGCCCTGGCCACACTGGGG
CTGCCTTTCTCTGACTCTGTCTTCCCCAAGTCAGGGGGCTCTCTGA
GTGCAGGGTCTGATGCTGAGTCCCACTTAGCTTGGGGTCAGAACCA
AGGGGTTTAATAAATAACCCTTGAAAACTGGA

SEQ ID NO:2—Amino Acid Sequence of Human Lrg1
[Sequences of SEQ ID NOS: 3-5 are Bold and Underlined within SEQ ID NO:2 below]

MSSWSRQRPKSPGGIQPHVSRTLFLLLLLAASAWGVTLSPKDCQ

VFRSDHGSSISCQPPAEIPGYLPADTVHLAVEFFNLTHLPANLL

QGASKLQELHLSSNGLESLSPEFLRPVPQLRVLDLTRNALTGLP

PGLFQASATLDTLVLKENQLEVLEVSWLHGLKALGHLDLSGNRL

RKLPPGLLANFTLLRTLDLGENQLETLPPDLLRGPLQLERLHLE

GNKLQVLGKDLLLPQPDLRYLFLNGNKLARVAAGAFQGLRQLDM

LDLSNNSLASVPEGLWASLGQPNWDMRDGFDISGNPWICDQNLS

DLYRWLQAQKDKMFSQNDTRCAGPEAVKGQTLLAVAKSQ

SEQ ID NOS: 3-5—Amino Acid Sequences of Peptides within Lrg1
SEQ ID NO:3—Amino Acids 1-24 of human Lrg1 from Appendix 2 (L94-117 from Appendix 3)

L1-24/L94-117:
LQELHLSSNGLESLSPEFLRPVPQ

SEQ ID NO:4—Amino Acids 169-192 of Human Lrg1 from Appendix 2 (L262-285 from Appendix 3)

L169-192/L262-285:
LDMLDLSNNSLASVPEGLWASLGQ

SEQ ID NO:5—Amino Acids 227-252 of human Lrg1 from Appendix 2 (L320-345 from Appendix 3)

L227-252/L320-345:
KMFSQNDTRCAGPEAVKGQTLLAVAK

---

The invention claimed is:

1. A method of inhibiting vasculoproliferation comprising administering to a patient in need thereof an effective amount of an antagonist of Lrg1, wherein said antagonist comprises a short interfering RNA (siRNA) that targets Lrg1 RNA to knock down Lrg1 expression and so reduce Lrg1 function.

2. The method according to claim 1, wherein the vasculoproliferation is selected from a group consisting of neovascularisation, vascular endothelial cell proliferation, angiogenesis, telangiectasia, diabetic retinopathy, retinal vein occlusion, retinopathy of prematurity, macular telangiectasia, age-related macular degeneration or choroidal neovascularization.

3. The method according to claim 1, wherein the Lrg1 antagonist is for use in combination with an antiangiogenic compound.

4. The method according to claim 3, wherein the antiangiogenic compound is an antagonist of vascular endothelial growth factor (VEGF).

5. The method according to claim 4, wherein the antagonist of VEGF is an anti-VEGF antibody.

6. The method according to claim 4, wherein the antagonist of VEGF is a receptor-based VEGF trap.

7. The method according to claim 4, wherein the antagonist of VEGF is Aflibercept.

8. The method according to claim 4, wherein the antagonist of VEGF is Avastin or Lucentis.

* * * * *